(12) United States Patent  
To et al.

(10) Patent No.: US 8,628,790 B2  
(45) Date of Patent: Jan. 14, 2014

(54) COATING SYSTEM AND METHOD FOR DRUG ELUTION MANAGEMENT

(75) Inventors: John Thao To, Newark, CA (US); Charles M. Blaha, San Francisco, CA (US)

(73) Assignee: PLS Technologies, LLC, Ambler, PA (US)

( * ) Notice: Subject to any disclaimer, the term of this patent is extended or adjusted under 35 U.S.C. 154(b) by 339 days.

(21) Appl. No.: 12/901,426

(22) Filed: Oct. 8, 2010

(65) Prior Publication Data

US 2011/0086081 A1  Apr. 14, 2011

Related U.S. Application Data

(60) Provisional application No. 61/250,471, filed on Oct. 9, 2009, provisional application No. 61/283,538, filed on Dec. 4, 2009, provisional application No. 61/324,903, filed on Apr. 16, 2010, provisional application No. 61/369,423, filed on Jul. 30, 2010.

(51) Int. Cl.
*A61F 13/00* (2006.01)
*A61F 2/00* (2006.01)
*A61F 2/04* (2013.01)

(52) U.S. Cl.
USPC .......... 424/423; 424/422; 424/426; 623/1.42; 623/1.46

(58) Field of Classification Search
USPC ................ 424/422, 423, 426; 623/1.42, 1.46
See application file for complete search history.

(56) References Cited

U.S. PATENT DOCUMENTS

| | | |
|---|---|---|
| 4,130,904 A | 12/1978 | Whalen |
| 4,739,762 A | 4/1988 | Palmaz |
| 4,776,337 A | 10/1988 | Palmaz |
| 4,878,906 A | 11/1989 | Lindemann et al. |
| 5,071,656 A | 12/1991 | Lee et al. |
| 5,123,917 A | 6/1992 | Lee |
| 5,288,711 A | 2/1994 | Mitchell et al. |
| 5,425,710 A | 6/1995 | Khair et al. |
| 5,464,650 A | 11/1995 | Berg et al. |
| 5,486,547 A | 1/1996 | Matsuda et al. |
| 5,516,781 A | 5/1996 | Morris et al. |
| 5,624,411 A | 4/1997 | Tuch |
| 5,624,450 A | 4/1997 | Glastra |
| 5,741,326 A | 4/1998 | Solovay |
| 5,904,698 A | 5/1999 | Thomas et al. |
| 5,961,545 A | 10/1999 | Lentz et al. |
| 6,060,474 A | 5/2000 | Williams et al. |
| 6,143,022 A | 11/2000 | Shull et al. |
| 6,383,171 B1 | 5/2002 | Gifford et al. |
| 6,585,764 B2 | 7/2003 | Wright et al. |
| 6,592,616 B1 | 7/2003 | Stack et al. |
| 6,626,861 B1 | 9/2003 | Hart et al. |
| 6,699,276 B2 | 3/2004 | Sogard et al. |
| 6,759,431 B2 | 7/2004 | Hunter et al. |
| 6,939,375 B2 | 9/2005 | Sirhan et al. |
| 6,939,376 B2 | 9/2005 | Shulze et al. |
| 7,060,319 B2 | 6/2006 | Fredrickson |
| 7,208,011 B2 | 4/2007 | Shanley et al. |
| 7,217,286 B2 | 5/2007 | Falotico et al. |
| 7,279,175 B2 | 10/2007 | Chen et al. |
| 7,341,630 B1 | 3/2008 | Pacetti |
| 7,517,352 B2 | 4/2009 | Evans et al. |
| 2002/0026145 A1 | 2/2002 | Bagaoisan et al. |
| 2002/0082679 A1 | 6/2002 | Sirhan et al. |
| 2003/0028244 A1* | 2/2003 | Bates et al. .................. 623/1.15 |
| 2004/0044404 A1 | 3/2004 | Stucke et al. |
| 2004/0138696 A1 | 7/2004 | Drasler et al. |
| 2005/0043780 A1 | 2/2005 | Gifford et al. |
| 2005/0049672 A1 | 3/2005 | Murphy |
| 2005/0055078 A1 | 3/2005 | Campbell |

OTHER PUBLICATIONS

Houchin et al., Journal of Pharmacuetical Sciences, Jul. 2008, 97(7), 2395-2404.*
Patent Cooperation Treaty, "International Search Report" in PCT Application No. PCT/US2010/052104, Document of 4 pages, dated Jul. 29, 2011.
Budhian, A., et al., "Production of haloperidol-loaded PLGA nanoparticles for extended controlled drug release of haloperidol" J. Microencapsul., 2005, vol. 22, pp. 773-785.
Acharya, G. & Park, K. "Mechanisms of controlled drug release from drug-eluting stents" Advanced Drug Delivery Reviews, 2006, vol. 58, pp. 387-401.
Patent Cooperation Treaty, "International Preliminary Report on Patentability" in PCT Application No. PCT/US2010/052104, Document of 7 pages, dated Apr. 11, 2012.

* cited by examiner

*Primary Examiner* — Abigail Fisher
(74) *Attorney, Agent, or Firm* — Akerman LLP; Richard P. Gilly

(57) ABSTRACT

The teachings are directed to a medical device having a drug-retaining coating that at least substantially delays the initial elution of a drug for a time effective at forming a functional endothelium over a surface of the medical device.

14 Claims, 6 Drawing Sheets

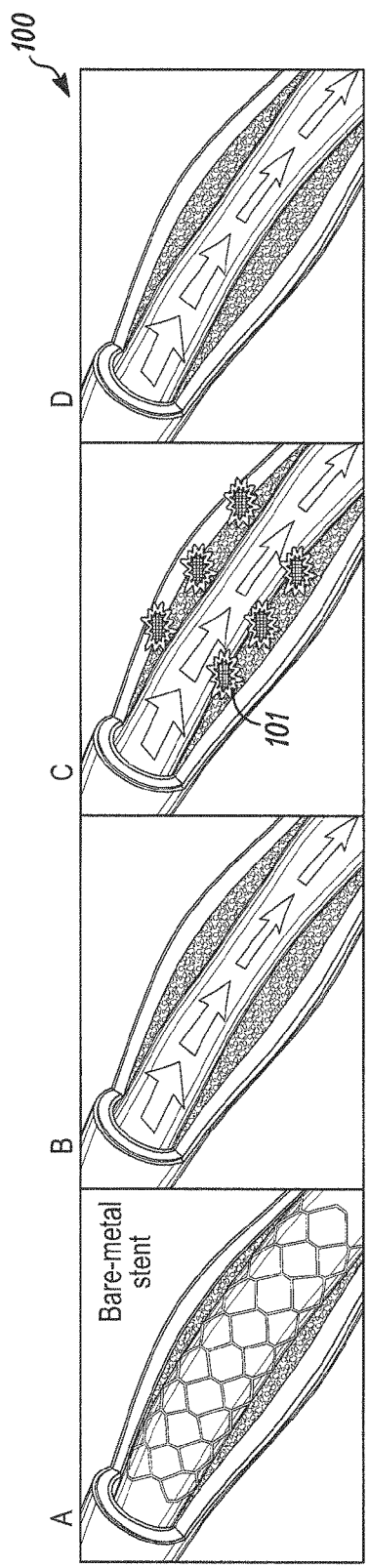
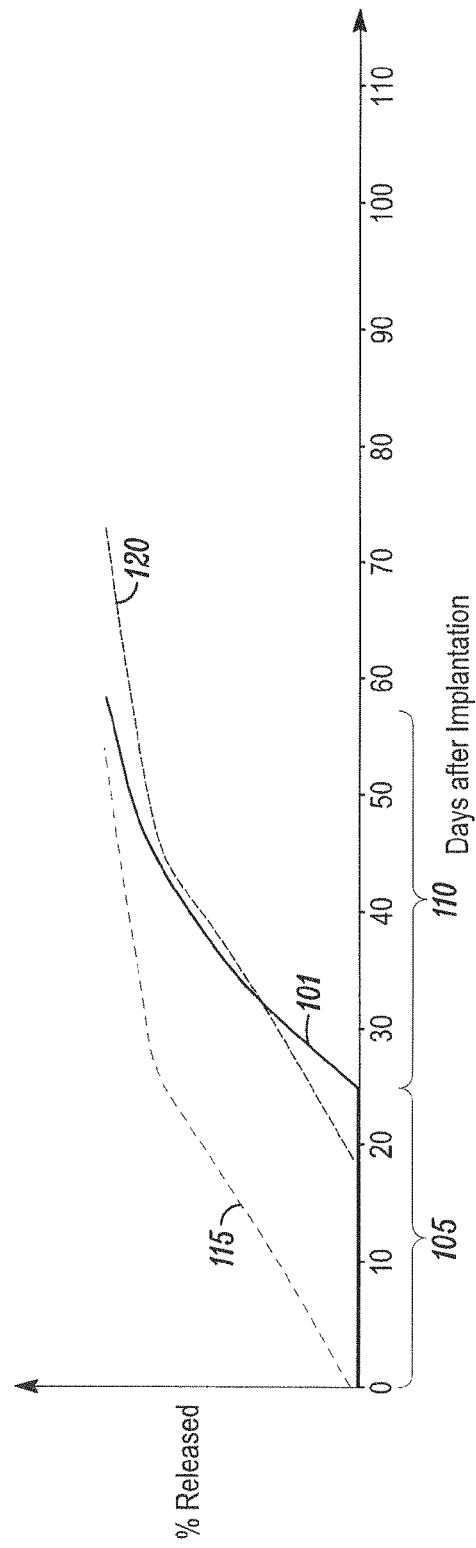
FIG. 1A
FIG. 1B

A  B

COATING SYSTEM AND METHOD FOR DRUG ELUTION MANAGEMENT

CROSS-REFERENCE TO RELATED APPLICATIONS

This application claims the benefit of U.S. Provisional Application Nos. 61/250,471, filed Oct. 9, 2009; 61/283,538, filed Dec. 4, 2009; 61/324,903, filed Apr. 16, 2010; and 61/369,423, filed Jul. 30, 2010; each of which is hereby incorporated herein by reference in its entirety.

BACKGROUND

1. Field of the Invention

The teachings are directed to a medical device having a drug-retaining coating that at least substantially delays the initial elution of a drug for a time effective at forming a functional endothelium over a surface of the medical device.

2. Description of the Related Art

Polymers and other materials have been utilized to control the release of drugs from coatings, capsules, tablets, and other platforms in the medical device industry. One of the challenges with drug elution into a biological system is the dosage and timing curve after deployment into such system.

Local delivery of agents is often preferred over systemic delivery of agents, particularly where high systemic doses are necessary to achieve an effect at a particular site within a subject, because high systemic doses of agents can often create adverse effects within the subject. One proposed method of local delivery includes coating the surface of a medical article with a polymeric carrier and attaching an agent to, or blending the agent with, the polymeric carrier. Some of the currently desired polymeric materials such as, for example, the poly(hydroxyalkanoates) are biodegradable.

In the cardiovascular stent field, an exhaustive number of configurations of drug eluting stents have been investigated to control the deposition of cellular material onto recently-deployed stent prostheses. It has been discovered over time that bare metal stents are likely to become covered with platelets, leukocytes, endothelial cells, smooth muscle cells ("SMC"), and fibrous tissue matrix after deployment within the cardiovascular system, such as in a cardiac artery. The platelet deposition, leukocyte recruitment, SMC proliferation, and matrix deposition responses have caused detrimental physiological effects within such a system such as compromised blood flow due to slow clogging of the stent (restenosis). In attempts to retain patency, or prevent restenosis, through such stent structures after deployment, various companies have developed composite stent prostheses comprising, in various forms, a bare metal stent coated with a drug-containing coating, the drug being one configured to prevent, at least transiently, the proliferation of tissues which may lead to partial or complete restenosis of the stent. Problems of thrombus formation and development of hyperproliferative tissue remain of great concern to those skilled in the art.

One problem is that an initial burst of drug, such as an anti-proliferative drug used to prevent restenosis, has caused unwanted biological responses, such as an inhibition of development of functional endothelium. The lack of functional endothelialization can render the stent vulnerable to blood clots (thrombosis) and can require that the patient remain on aggressive anti-thrombogenic drug therapy to prevent blood clots. As such, one of skill would appreciate a coating system that facilitates formation of a functional endothelium, soon after implantation, as a source of thrombomodulin, a natural anti-clotting protein. Another problem is the development of hyperproliferative tissue. Avoiding the use of an anti-proliferative may provide the functional endothelium but, unfortunately, the formation of excess hyperproliferative tissue can result in a potentially harmful restenosis in vascular applications, for example, a condition including an excessive deposition and/or proliferation of tissue in the region of the implant. Finally, the anti-proliferative drug can also be lost to the blood stream or surrounding causing side effects if released too soon and there would be lack of drug to be effective at a later time point after implantation when unwanted tissue hyperproliferation occurs. Since these issues are not isolated to cardiovascular drug-eluting stents, one of skill in the art of implantable medical devices would appreciate having such an enhanced control over drug elution for a variety of applications, including simple ingested, injected or implanted medications, and coated prosthetic platforms, such as stents, screws, pellets, and the like.

Accordingly, there is a need for coatings (i) that have sufficient mechanical properties for applications that can benefit from biodegradable polymers, (ii) that can release agents after formation of a functional endothelium that provides a localized source of thrombomodulin, (iii) that can be designed to have a predetermined release rate and absorption rate to inhibit the formation of hyperproliferative tissue; and (iv) that can be combined with agents that are not only bioactive and/or biobeneficial but also control a physical property and/or a mechanical property of a medical article formed from the polymer.

SUMMARY

The teachings are generally directed to an improved drug-eluting medical device such as, for example, a stent. In some embodiments, the teachings are directed to a medical device having a drug-retaining coating that at least substantially delays the initial elution of a drug for a time effective at forming a functional endothelium over a surface of the medical device. In these embodiments, the coating comprises a drug-containing layer applied over a surface of the medical device, the drug-containing layer having a drug that functions as an anti-proliferative agent; and a drug-reservoir layer applied over the drug-containing coating, the drug reservoir layer comprising a drug-retaining layer that is void or substantially void of the drug at a time of implantation in a subject. The coating can at least substantially promote development of a functional endothelium as a source of thrombomodulin when compared to a control development of such endothelium formation observed following implantation of a metal or polymer drug-eluting medical device; and, the coating can at least substantially inhibit development of a hyperproliferative tissue when compared to a control development of such hyperproliferative tissue observed following implantation of a metal or polymer medical device that does not elute a drug.

In some embodiments, the teachings are directed to a method of inhibiting the formation of hyperproliferative tissue and promoting the formation of a functional endothelium after implantation of a medical device in a subject. In these embodiments, the method comprises obtaining the device described above; and, implanting the device in the subject.

In some embodiments, the teachings are directed to a therapeutic coating that promotes formation of a functional endothelium on a medical device. In these embodiments, the coating comprises a biodegradable drug-containing layer that is positioned over a surface of a medical device and serves as a source of a drug that functions as an anti-proliferative agent in a subject. The coating also comprises a biodegradable drug-reservoir layer positioned over a surface of the drug-containing layer. The drug-reservoir layer comprises a drug-retaining layer, wherein the drug-retaining layer is void or substantially void of the drug at a time of implantation in the subject and functions to retain and at least substantially block an initial release of the drug into the subject for a time sufficient to form a functional endothelium over the surface of the medical device. In these embodiments, the functional endothelium can provide a source of thrombomodulin to the subject. It should be appreciated that the drug may be at least substantially miscible in the drug-reservoir layer to facilitate a retention of the drug. It should be appreciated that the time sufficient to form a functional endothelium may vary according to selection of subject, medical device, location of an implant, materials used, and the like. In some embodiments, the time can be at least about 20 days.

In some embodiments, the drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons. And, in some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

Moreover, the drug-retaining layer can comprise a polymer having ester-terminal groups. The polymer can have, for example, a molecular weight ranging from about 50 KDaltons to about 190 KDaltons, and a structure that remains at least substantially undegraded during the initial release of the drug, the structure comprising P—$CO_2$R, where P is the polymer backbone and R is an alkyl group having from 1 to 4 carbons.

The coating may at least substantially promote development of the functional endothelium as the source of the thrombomodulin when compared to a control development of such endothelium formation observed following implantation of a metal or polymer drug-eluting medical device. In addition, the coating may at least substantially inhibit development of a hyperproliferative tissue when compared to a control development of such hyperproliferative tissue observed following implantation of a metal or polymer medical device that does not elute a drug. In some embodiments, the medical device comprises a stent.

The coatings can be designed for a delay time before onset of the release of the drug and elution of the drug at a certain rate. In some embodiments, the drug-reservoir layer can further comprise an accelerant layer to accelerate the onset of elution. And, in some embodiments, the accelerant layer having a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons. In some embodiments, the accelerant layer can comprise a drug. The amount of drug in the accelerant layer can be 0, 5, 10, 15, 20, 25, 30, 35, 40, 45, 50, 60 percent, or any amount therein.

In fact, other variables can be used to design for a desired delay time and release rate of the drug. In some embodiments, for example, the thickness ratio of the drug-reservoir layer to the drug-containing layer can range from about 4:1 to about 10:1, and the miscibility of the drug in a coating can be preselected to affect the rate of drug migration. In some embodiments, the thickness of the coating can range from about 2 microns to about 9 microns. And, in some embodiments, the thickness ratio of the drug-retaining layer to the drug-containing layer ranges from about 4:1 to about 7:1.

As such, the teachings are generally directed to a method of inhibiting the formation of hyperproliferative tissue and promoting the formation of a functional endothelium after implantation of a medical device in a subject. The method can comprise applying a therapeutic coating on a medical device and implanting the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of implantation in the subject and functioning to retain and at least substantially block an initial release of the drug into the subject for a time sufficient to form a functional endothelium over the surface of the medical device, the functional endothelium providing a source of thrombomodulin to the subject.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. In some embodiments, the drug-reservoir layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-reservoir layer, is more hydrophilic than the remainder of the drug-reservoir layer, and comprises at least one sub-layer having a thickness of less than or equal to 3 microns, where a repeated application the sub-layer is used to form thicknesses of greater than 3 microns. The application of the sub-layers can be used to at least substantially promote a retention of the drug in the drug-containing layer during formation of the coating when compared to such a coating without the application of the sub-layers.

The coatings taught herein can, in some embodiments, further comprise pockets of hydrophilic material in the drug-retaining layer, wherein the hydrophilic material comprises a component selected from the group consisting of dextran, heparin, ticlopidine, chlopidogrel, enoxaparin, dalteparin, hirudin, bivalirudin, argatroban, and danparoid. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, estradiol, and transcription factor E2F1.

BRIEF DESCRIPTION OF THE FIGURES

FIG. 1 illustrates an elution profile from a coating design, wherein the elution is expressed in terms of fractional release vs. time after implantation, according to some embodiments.

DETAILED DESCRIPTION OF THE INVENTION

Figure 2:
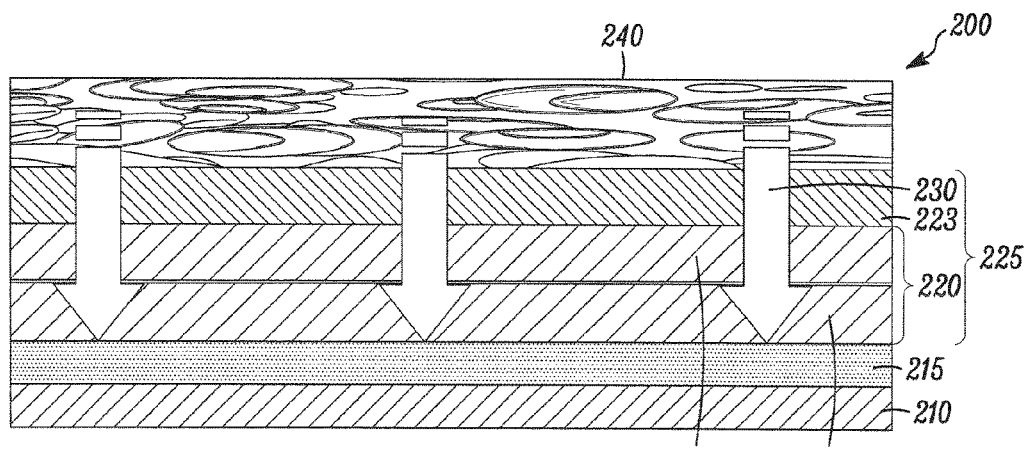
FIG. 2 illustrates a coated device upon implantation in a subject, according to some embodiments.

The teachings provided herein are generally directed to an improved drug-eluting medical device such as, for example, a stent. In some embodiments, the teachings are directed to a medical device having a drug-retaining coating that at least substantially delays the initial elution of a drug for a time effective at forming a functional endothelium over a surface of the medical device. In some embodiments, the coatings are a switch for "turning on" drug elution at a desired time, where the switch can be programmed through coating design to elute at the desired time using the methods taught herein. In some embodiments, the coating can be designed to elute at a desired rate after the onset of elution.

Merely forming an endothelium is not the same as forming a functional endothelium. The term "functional endothelium" includes, for example, an endothelium that functions to at least provide a localized source of thrombomodulin, nitric oxide, or a combination thereof. On a functional endothelium, for example, there is typically an abundance of thrombomodulin, a protein that inhibits blood clot formation. Besides the benefits of thrombomodulin in reducing blood clots, there are several other benefits of a functional endothelium. A functional endothelium, for example, can also inhibit hyperproliferative tissue growth long term or produce nitric oxide that can allow the blood vessels to dilate to accommodate increased blood flow from exercise for example.

In some embodiments, a coating "at least substantially delays the initial elution" includes, for example, where there is no measurable elution of drug for an initial period of time, or the elution of drug over the initial period of time is negligible or sufficiently retained, such that the desired effect that would be obtained in the absence of any drug elution is still obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. And, "a time effective at forming a functional endothelium over a surface of the medical device" can be, for example, any duration of time in which the elution of drug can be entirely or partially inhibited to allow for formation of an endothelium that provides a localized source of thrombomodulin where desired, in an area of an implant. In some embodiments, the terms "block", "delay", and "retain" can be used interchangeably.

The coating can comprise a drug-containing layer applied over a surface of the medical device. In some embodiments, the drug-containing layer can be 100% drug. In some embodiments, the drug-containing layer can comprise 5, 10, 15, 20, 25, 30, 35, 40, 45, 50, 55, 60, 65, 70, 75, 80, 85, 90, 95, 99, 100 percent drug, or any amount therein.

The surface of the medical device can include any surface of a medical device, such as an implanted medical device. The surface may be, for example, an abluminal or luminal surface of a stent, in some embodiments. The drug-containing layer can be used to provide a drug that functions as an anti-proliferative agent; and, a drug-reservoir layer can be applied over the drug-containing coating.

In some embodiments, the drug reservoir layer can comprise a drug-retaining layer that is void or substantially void of the drug at a time of implantation in a subject. A layer can be considered "substantially void" of the drug where the layer has an almost immeasurable amount of drug in the layer, or the amount is so small that the effect on the delay in onset of drug elution is still controllable using the coatings and methods taught herein. In some embodiments, a layer is substantially void of the drug, where the amount of drug is negligible or sufficiently small, such that the desired effect of the delay in the onset of elution would be obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. In some embodiments, a layer is substantially void of drug where the drug composes less than 2.0, 1.0, 0.8, 0.6, 0.5, 0.4, 0.3, 0.2, 0.1, 0.09, 0.08, 0.07, 0.05, 0.03, 0.01, 0.001 percent of the layer, or any amount therein.

And, in some embodiments, the coating can at least substantially promote development of a functional endothelium, the functional endothelium providing an additional a source of thrombomodulin when compared to a control development of an endothelium formation observed following implantation of a metal or polymer drug-eluting medical device. Moreover, in some embodiments, the coating can at least substantially inhibit development of a hyperproliferative tissue when compared to a control development of such hyperproliferative tissue observed following implantation of a metal or polymer medical device that does not elute a drug. As such, the teachings are also directed to a method of inhibiting the formation of hyperproliferative tissue and promoting the formation of a functional endothelium after implantation of a medical device in a subject. Moreover, the teachings also provide a method of obtaining one of the devices taught herein and implanting the device in a subject.

FIG. 1 illustrates an elution profile from a coating design, wherein the elution is expressed in terms of fractional release vs. time after implantation, according to some embodiments. A variety of factors in the stent implant response 100 is illustrated in FIG. 1 through a correlation between onset and extent of drug elution 101, extent of endothelialization 115, and the extent of the development of hyperproliferative tissue 120 as the implant procedure progresses from the time of implantation, time 0.

FIG. 1A illustrates the state of the implant in vivo at time 0, a time at which the implant enters the subject and the subject begins to respond biologically to the implant. FIG. 1B illustrates the state of the implant during a time of endothelialization following implantation, a time at which the biological response of endothelialization and hyperproliferation of tissue actively take place as a response to the implant and in the absence of elution of a drug per the methods taught herein. FIG. 1C illustrates that this particular coating is designed to initiate elution of an anti-proliferative drug 101 at around day 25, a time that was preselected as a time effective at forming a functional endothelium over a surface of the medical device. In this illustration, the onset of elution of the drug was delayed for the 25 days to allow for a beneficial development of the "functional" endothelium, a tissue that provides a source of thrombomodulin to an area affected by the implant.

As can be seen, the initiation of elution of the drug 101 created a marked inflexion in the rate of endothelialization and, more specifically, a marked reduction in the rate of endothelization, a response that would prevent formation of a functional endothelium if the drug release was not at least substantially blocked for the time sufficient to form the functional endothelium. In some embodiments, the first 20 days of functional endothelialization can be the most active period, for example, such that at least substantially blocking drug release for 20 day can be sufficient in these embodiments. After the formation of a functional endothelium, the anti-proliferative drug can be released to inhibit hyper-proliferative tissue growth, also most active at around 20 days in some embodiments, leaving the device with a thin layer of functional endothelium that provides the source of thrombomodulin to the area affected by the implant.

FIG. 2 illustrates a coated device upon implantation in a subject, according to some embodiments. The coated device 200 has a frame 210, a drug-containing 215 on a surface of the frame 210, a drug reservoir layer 225, an optional accelerant layer 220, and an optional sub-layering 223 of the drug reservoir layer. The illustration shows water ingress 230 that can occur after implantation, an effect that can cause physical and/or chemical changes to the coating while implanted in contact with tissue 240.

Figure 3:
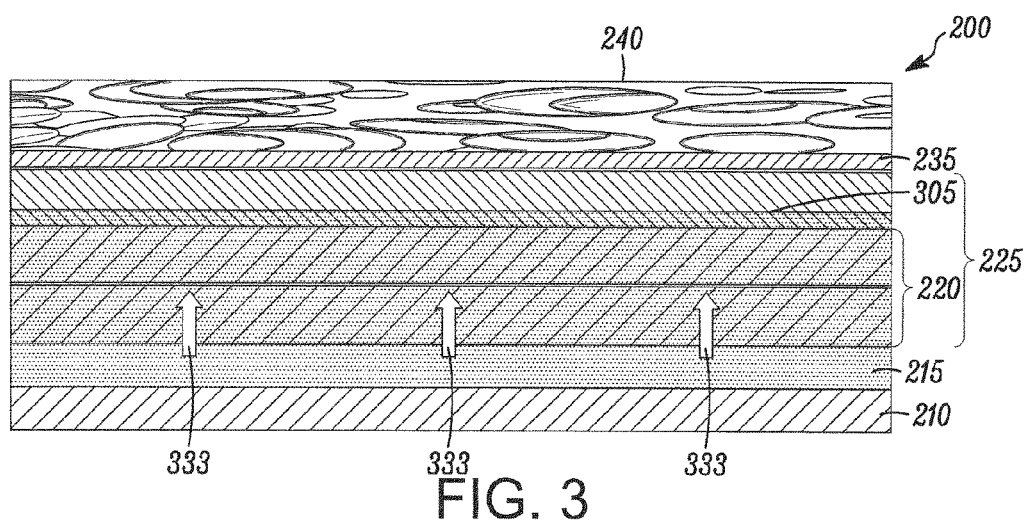
FIG. 3 illustrates the migration of a drug through a therapeutic coating, according to some embodiments.
Figure 4:
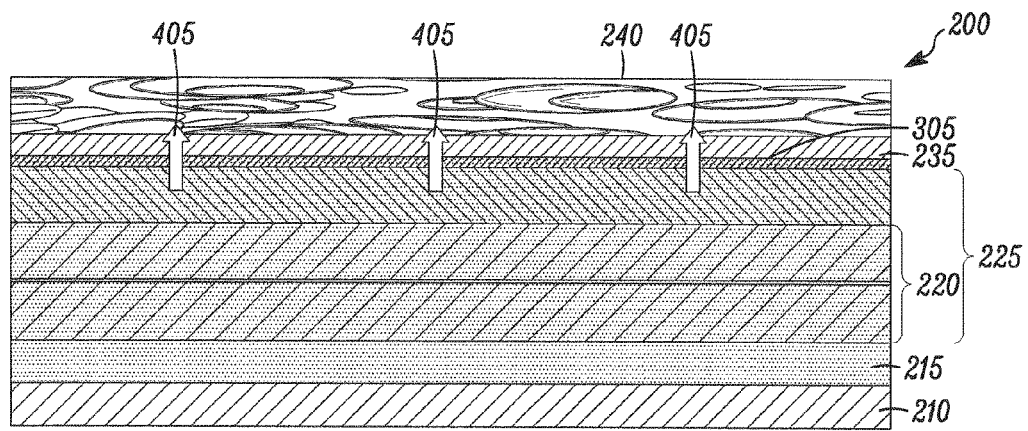
FIG. 4 illustrates the filling of a drug reservoir layer in vivo, according to some embodiments.

FIG. 3 illustrates the migration of a drug through a therapeutic coating, according to some embodiments. The drug 305 migrates 333 from the drug-containing layer 215 in the drug reservoir 225 during the delay phase 105, a period in which the functional endothelium 235 starts to form following implantation of the device. FIG. 4 illustrates the filling of a drug reservoir layer in vivo, according to some embodiments. The drug-reservoir layer 225 becomes filled by migration of the drug from the drug-containing layer 215 into the drug-reservoir layer 225, and the coating adapts to release 405 the drug 305 into the surrounding tissue 240 in an area affected by the implant.

As such, given the above, the teachings are naturally directed to include a therapeutic coating that promotes formation of a functional endothelium on a medical device. The coating comprises a biodegradable drug-containing layer that is positioned over a surface of a medical device and serves as a source of a drug that functions as an anti-proliferative agent in a subject. The coating can also comprise a biodegradable drug-reservoir layer positioned over a surface of the drug-containing layer. The drug-reservoir layer can comprise a drug-retaining layer, wherein the drug-retaining layer can be void or substantially void of the drug at a time of implantation in the subject and function to retain and at least substantially block an initial release of the drug into the subject for a time sufficient to form a functional endothelium over the surface of the medical device. As discussed, the functional endothelium can provide a beneficial source of thrombomodulin to the subject to an area affected by a medical device.

It should be appreciated that, in the embodiments taught herein, the drug may be selected by its miscibility in a preselected polymer matrix. For example, the drug may be selected because it is at least substantially miscible in the drug-reservoir layer in order to retain the drug for a desired amount of time. Or, the drug may be miscible to a preselected degree, an amount sufficient to facilitate a desired retention time of the drug. A desired retention time is facilitated, for example, in a case where a functional endothelium has formed to a desired extent. It should be appreciated that the desired retention time is facilitated where the retention time is modulated to a desired amount, and the modulation of the time can include an increase or a decrease in the retention time through altering one or more coating variables, as described herein. One of skill should appreciate, for example, that miscibility of the drug with the polymer is a variable that can modulate an affinity of the drug for the polymer, in some embodiments, thus affecting retention time.

In some embodiments, the drug and polymer are mixed or blended in solution, and one skill will appreciate that the mixes or blends can be considered substantially miscible, for example, where they mix or blend homogeneously in the desired proportions of drug to polymer, at least for the purposes of the teachings provided herein. In contrast, the mixes or blends may be considered immiscible, at least for the purposes of the teachings provided herein, where the mix or blend of polymer and drug is not homogeneous in the mix or blend in the proportions desired. In some embodiments, a drug can be considered substantially miscible in a polymer, where a homogeneous, saturated solution comprising the drug in a solvent spreads on a layer of the polymer, such that (i) the solution of the drug in the solvent has a contact angle of greater than 90 degrees on the surface of the polymer; and (ii) the layer of the polymer was formed used the same solvent. In some embodiments, the drug is substantially miscible in the polymer where the surface tension of the drug and the surface tension of the polymer are the same or similar when compared using the same solvent. A surface tension is the same, where the difference is not statistically significant, and similar, where the surface tension does not vary by more than 1, 2, 3, 4, 5, 10, 15, 20, 25, or 30 percent, in some embodiments. It should be appreciated, however, that any method known to one of skill can be used to determine the relative degree of miscibility and affinity between the drug and the polymer.

In some embodiments, the retention time of a drug can be a time sufficient amount, or an otherwise desired amount of time, chosen based on any number of parameters recognized and known to one of skill in the art of drug elution from implanted medical devices. Such parameters can vary the desired amount of time based on, for example, type of implant, location of implant, construction of implant, selection of drug, desired effect, and the like.

It should be appreciated that the "time sufficient to form a functional endothelium" may vary according to selection of subject, medical device, location of an implant, materials used, and the like. In some embodiments, the time can be at least about 20 days. In some embodiments, a sufficient amount of time can range from about 5 days to about 120 days, from about 10 days to about 90 days, from about 12 days to about 50 days, from about 14 days to about 45 days, from about 15 days to about 90 days, from about 20 days to about 60 days from about 25 days to about 45 days, from about 20 days to about 40 days, from about 20 days to about 30 days, from about 25 days to about 35 days, or any range therein.

The Polymeric Compositions

The polymeric compositions taught herein include any desired polymer, combination of polymers, copolymers and agents known to one of skill to be useful as a medical device, or coating, as taught herein. These polymers can be biodegradable due to their labile nature, such as the labile nature of the ester groups that are present in some polymers. In some embodiments, these compositions can be designed such that they can be broken down, absorbed, resorbed and eliminated by a mammal. As such, the compositions can be used, for example, to form medical articles and coatings.

The terms "combine," "combined," and "combining" all refer to a relationship between components of a composition and include blends, mixtures, linkages, and combinations thereof, of components that form the compositions. The linkages can be connections that are physical, chemical, or a combination thereof. Examples of physical connections include, but are not limited to, an interlinking of components that can occur, for example, in interpenetrating networks and chain entanglement. Examples of chemical connections include, but are not limited to, covalent and noncovalent bonds. Covalent bonds include, but are not limited to, simple covalent bonds and coordinate bonds. Non-covalent bonds include, but are not limited to, ionic bonds, and inter-molecular attractions such as, for example, hydrogen bonds and attractions created by induced and permanent dipole-dipole interactions.

Compositions that are selected for an in vivo use should meet particular requirements with regard to physical, mechanical, chemical, and biological properties of the compositions. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing. An example of a chemical property that can affect performance of a biodegradable composition in vivo is the rate of absorption of the composition by a subject. An example of a biological property that can affect performance of a composition in vivo is the bioactive and/or biobeneficial nature of the composition, While not intending to be bound by any theory or mechanism of action, water uptake by a composition can be an important characteristic in the design of a composition. Water can act as a plasticizer for modifying the mechanical properties of the composition. Control of water uptake can also provide some control over the hydrolysis of a coating and thus can provide control over the degradation rate, absorption rate, and the agent release rate of a medical article or coating in vivo, such as for the release of a drug. In some embodiments, an increase in hydrolysis can also increase the release rate of an agent by creating channels within a medical article or coating that can serve as transport pathways for diffusion of the agents from the composition. The terms "subject" and "patient" can be used interchangeably and refer to an animal such as a mammal including, but not limited to, non-primates such as, for example, a cow, pig, horse, cat, dog, rat, and mouse; and primates such as, for example, a monkey, or a human.

In some embodiments, the compositions may be used, for example, to form medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and absorption rate; and (iv) that can be combined with agents that are not only bioactive and/or biobeneficial but also control a physical property and/or a mechanical property of a medical article or coating formed from the polymer.

A polymer or coating can be "biodegradable," for example, when it is capable of being completely or substantially degraded or eroded when exposed to an in vivo environment or a representative in vitro environment. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation. The terms "bioabsorbable" and "biodegradable" are used interchangeably in this application. The polymers used in the teachings herein may be biodegradable and may include, but are not limited to, condensation copolymers. In some embodiments, the drug-containing layer can comprise a poly (lactic-co-glycolic acid), a monomer ratio of lactic acid to glycolic acid ranges from about 85:15 to about 50:50, and a molecular weight ranging from about 90 KDaltons to about 160 KDaltons.

Biodegradable polymers can be used, and biodegradable polymers should be selected according to their behavior and hydrolysis in vivo. In some embodiments, the number average molecular weight of the polymer fragments should be at or below about 40,000 Daltons, or any range therein. In some embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

Examples of polymers that can be used in some embodiments include, but are not limited to, poly(acrylates) such as poly(butyl methacrylate), poly(ethyl methacrylate), poly(hydroxylethyl methacrylate), poly(ethyl methacrylate-co-butyl methacrylate), copolymers of ethylene-methyl methacrylate; poly(2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; fluorinated polymers or copolymers such as poly (vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly (phosphoester urethane); poly(trimethylene carbonate); poly (iminocarbonate); poly(ethylene); poly(propylene) co-poly (ether-esters) such as, for example, poly(dioxanone) and poly (ethylene oxide)/poly(lactic acid); poly(anhydrides), poly (alkylene oxalates); poly(phosphazenes); poly(urethanes); silicones; poly(esters); poly(olefins); copolymers of poly (isobutylene); copolymers of ethylene-alphaolefin; vinyl halide polymers and copolymers such as poly(vinyl chloride); poly(vinyl ethers) such as poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; poly(amides) such as Nylon 66 and poly(caprolactam); alkyd resins; poly (carbonates); poly(oxymethylenes); poly(imides); poly(ester amides); poly(ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and derivatives, analogs, homologues, congeners, salts, copolymers and combinations thereof. In some embodiments, other polymers may be selected such that they specifically exclude any one or any combination of these polymers.

In some embodiments, the coatings can comprise one or more biodegradable polymers. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the biodegradable polymers include, but are not limited to, polyesters, poly(ester amides); amino acids; PEG and/or alcohol groups, polycaprolactones, poly(L-lactide), poly(D,L-lactide), poly (D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly (amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof. In some embodiments, the polymers can include poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the polymers are selected such that they specifically exclude any one or any combination of these polymers.

In some embodiments, the polymers can be chemically connected by covalent bonds. In some embodiments, the polymers can be chemically connected to by non-covalent bonds such as, for example, by ionic bonds, inter-molecular attractions, or a combination thereof. In some embodiments, the polymers can be physically connected. In some embodiments, the polymers can be chemically and physically connected. Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed.

The behavior of the polymer matrix can be changed through selection of any number of factors that provide the desired drug elution, chemical and physical characteristics of the coatings taught herein. For example, the terminal end groups can be designed to contribute to imparting such characteristics in the polymers. A more hydrophilic end-group can increase the rate of ingress of water, for example, and likewise increase the rate of hydrolysis of the polymer chains, at least in some embodiments. Likewise, a less hydrophilic group can deter in the ingress of water, and slow the rate of hydrolysis, at least in some embodiments.

It should be appreciated that a polymer can be selected to have acid terminal end-groups, hydroxyl terminal end-groups, alkyl-ester end-groups, or a combination thereof. Moreover, a polymer layer can be created using sub-layers, where the layer can have a sub-layer having acid groups, a sub-layer having hydroxyl groups, a sub-layer having ester end-groups, or a combination thereof. In fact, the construction of the layers and sub-layers can be designed based on thickness ratios to design a coating that provides a desired characteristic or set of characteristics including, but not limited to, drug-retention time, a desired rate of hydrolysis, a desired glass transition temperature, a desired drug-elution rate, a desired toughness, a desired elasticity, a desired modulus, or a combination thereof.

Molecular weights can also be selected for the polymer in a particular layer or set of layers in the coating, as a mixture of molecular weights in a particular layer or set of layers, or as a set of sub-layers, where each layer in the sub-layer can have an independently selected molecular weight, mixture of molecular weights, or a combination thereof, where the molecular weight or mixture of molecular weights can be the same or different for each sub-layer. And, in many embodiments, a desired characteristic is that the polymers have a structure that remains at least substantially undegraded during the initial release of the drug. In some embodiments, for example, the drug-retaining layer can comprise a polymer having ester-terminal groups.

In some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

The molecular weights can be selected and tailored for a particular polymer selection and for a particular coating layer and purpose. For example, the polymer can have a molecular weight ranging from about 50 KDaltons to about 190 KDaltons, from about 50 KDaltons to about 190 KDaltons, from about 50 KDaltons to about 180 KDaltons, from about 60 KDaltons to about 170 KDaltons, from about 70 KDaltons to about 160 KDaltons, from about 80 KDaltons to about 150 KDaltons, from about 90 KDaltons to about 140 KDaltons, from about 90 KDaltons to about 160 KDaltons, from about 100 KDaltons to about 160 KDaltons, or any range therein.

Without intending to be bound by any theory or mechanism of action, in some embodiments, the drug-reservoir layer is initially implanted in a "drug-absorbing" state and is later transformed into a "drug-release" state over time due to changes in the physical and chemical structure across the coating in vivo. In the drug-absorbing state, the drug-reservoir layer has the highest affinity for the drug. In the drug-release state the drug-reservoir layer has a substantially lower affinity for the drug. The drug can have the highest solubility in the drug-reservoir layer in the drug-absorbing state and in the drug-release state, the drug can have a substantially lower solubility in the drug-reservoir layer. In some embodiments, the drug-absorbing state can reflect the state in which the glass transition temperature (Tg) of the drug-reservoir layer is higher than the temperature of the surrounding tissue/fluid, and the drug-release state can reflect the state at which the Tg of drug-reservoir layer is equal to or less than that of surrounding tissue/fluid. In some embodiments, coating has a Tg above the surrounding tissue temperature of 37 degrees C.

The polymer end-groups can have any structure known to one of skill that will provide the desired polymer characteristics for a particular coating layer or set of layers. In some embodiments, the end-group can be an ester-terminal group. For example, the polymer structure can comprise P—$CO_2$R, where P is the polymer backbone and R can be an alkyl group having from 1 to 4 carbons, from 1 to 20 carbons, from 2 to 12 carbons, from 1 to 10, from 2 to 8, from 1 to 6 carbons, from 1 to 5 carbons, or any range therein. In some embodiments, R can be any end-group known to one of skill, with the limitation that R cannot affect usefulness of the polymer, for example, the ability of the polymer to be applied as a coating on a desired medical device. In some embodiments, R can be saturated, unsaturated, aromatic, aliphatic, or any combination thereof.

In some embodiments, an R group can be a H; an aliphatic hydrocarbon group such as, for example, an alkyl, alkenyl, or alkynyl group; an aromatic group such as, for example, an aryl, aralkyl, aralkenyl, of aralkynyl group; various other groups as defined herein, or a combination thereof.

In some embodiments, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 4 to about 200 carbon atoms, from about 6 to about 150 carbon atoms, from about 12 to about 120 carbon atoms, from about 18 to about 90 carbon atoms, from about 24 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, isooctyl, nonyl, decyl, and the like; lower alkylene such as, for example, ethylene, propylene, propylyne, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms is replaced by a functional group, or the alkyl groups can contain an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain including at least one alkene functionality. The term "alkynyl" refers to a straight-chained or branched carbon-containing chain including at least one alkyne functionality. The term "aryl" refers to a carbon-containing ring bearing a system of conjugated double bonds often comprising at least six π (pi) electrons. Examples of aryl groups include, but are not limited to, phenyl, naphthyl, anysyl, toluoyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of side chains having 1 or more carbon atoms. In some embodiments, a radical is straight-chained if it has less than 0.01 mole percent of such side chains. In some embodiments, a radical is straight-chained if it has less than 0.001 mole percent of such side chains. A radical is "branched" when it has more than 0.1 mole percent of side chains having 1 or more carbon atoms. In some embodiments, a radical is branched when it has more than 0.01 mole percent of such side chains. In some embodiments, a radical is branched when it has more than 0.001 mole percent of such side chains.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted. Examples of substituents in substituted radicals include, but are not limited to, hydroxyls, alkyls, carboxyls, esters, aminos, amidos, iminos and combinations thereof. Such a functional group can also, for example, contain a heteroatom. Examples of heteroatoms of the hetero-radicals include, but are not limited to, sulfur, phosphorous, oxygen, nitrogen and combinations thereof.

In some embodiments, the functional groups can include, but are not limited to, oxygen-containing groups such as, for example, alcohols, ethers, phenols, and derivatives thereof. Such oxygen-containing groups include, but are not limited to, acetonides, alcohols, alkoxides, bisphenols, carbinols, cresols, diols, enols, enolates, epoxides, ethers, glycols, hydroperoxides, peroxides, phenols, phenolates, phenoxides, pinacols, trioxides, and ynols.

In some embodiments, the functional groups can include, but are not limited to, oxygen-containing groups such as, for example, aldehydes, ketones, quinones and derivatives thereof. Such oxygen-containing groups include, but are not limited to, acetals, acyloins, aldehydes, carbonyl compounds, diosphenols, dypnones, hemiacetals, hemiketals, ketals, ketenes, keto compounds, ketones, quinhydrones, quinomethanes, quinines, and combinations thereof.

In some embodiments, the functional groups can be oxygen-containing groups including, but not limited to, carboxylic acids, oxoacids, sulfonic acids, acid anhydrides, acid thioanhydrides, acyl groups, acyl halides, acylals, anhydrides, carboxylic acids, cyclic acid anhydrides, cyclic anhydrides, esters, fulgides, lactides, lactols, lactones, macrolides, naphthenic acids, ortho acids, ortho esters, oxo carboxylic acids, peroxy acids, and combinations thereof.

In some embodiments, the functional groups can include, but are not limited to, nitrogen-containing groups containing one nitrogen such as, for example, aldimines, aldoximes, alkoxyamines, amic acids, amides, amines, amine oxides, amine ylides, carbamates, hemiaminals, carbonitriles, carboxamides, isocyanides, cyanates, isocyanates, diisocyanates, cyanides, cyanohydrins, diacylamines, enamines, fulminates, hemiaminals, hydroxamic acids, hydroximic acids, hydroxylamines, imides, imidic acids, imidines, imines, oximes, isoureas, ketenimines, ketimines, ketoximes, lactams, lactims, nitriles, nitro, nitroso, nitrosolic acids, oxime O-ethers, quaternary ammonium compounds, quinone imines, quinonoximes, azomethines, ureides, urethanes, and combinations thereof.

In some embodiments, the functional groups can include, but are not limited to, nitrogen-containing groups containing two or more nitrogens such as, for example, aldazines, amide hydrazones, amide oximes, amidines, amidrazones, aminals, amine imides, amine imines, isodiazenes, azans, azides, azo imides, azines, azo compounds, azomethine imides, azoxy compounds, carbodiimides, carboxamidines, diamidides, diazo compounds, diazoamino compounds, diazoates, diazooxides, formamidine disulfides, formazans, hydrazides, hydrazide hydrazones, hydrazide imides, hydrazidines, hydrazines, hydrazo compounds, hydrazones, ketazines, nitramines, nitrile imines, nitrimines, nitrolic acids, nitrosamides, nitrosamines, nitrosimines, ortho amides, semicarbazones, semioxamazones, triazanes, triazenes, and combinations thereof.

In some embodiments, the functional groups can include, but are not limited to, sulfur-containing groups such as sulfones, sulfides, sulfinamides, sulfilimines, sulfimides, sulfinamides, sulfinamidines, sulfines, sulfinic acids, sulfinic anhydrides, sulfinylamines, sulfonamides, sulfones, sulfonediimines, sulfonic acids, sulfonic anhydrides, sulfoxides, sulfoximides, sulphur diimides, thio, thioacetals, thioaldehydes, thioanhydrides, thiocarboxylic acids, thiocyanates, thioether, thiohemiacetals, thioketones, thiol, thiolates, xanthic acids, and combinations thereof.

In some embodiments, the functional groups can include, but are not limited to, silyl groups, halogens, selenoethers, trifluoromethyls, thio-derivatives of urethanes where at least one oxygen atom is replaced by a sulfur atom, phosphoryls, phosphonates, phosphinates, and combinations thereof. In some embodiments, the functional groups are capable of free-radical polymerization and can include, but are not limited to, ethylenically unsaturated groups such as, for example, allyl, vinyl, acryloyl and methacrylol, and maleate and maleimido; and combinations thereof. In some embodiments, the functional groups include halides. In some embodiments, the functional group may include light scattering groups, magnetic groups, nanogold, other proteins, a solid matrix, radiolabels, carbohydrates, and combinations thereof.

The coating may at least substantially promote development of the functional endothelium as the source of the thrombomodulin when compared to a control development of such endothelium formation observed following implantation of a metal or polymer drug-eluting medical device. In some embodiments, the medical device comprises a stent.

One of skill will appreciate that a functional endothelium exists, or is promoted, for example, where the amount of thrombomodulin in the functional endothelium is in a quantity sufficient to show a statistical difference in an amount of thrombus formation when compared to a control development of such an endothelium, or lack thereof, observed following implantation of a control metal or polymer drug-eluting device. In some embodiments, the functional endothelium has been promoted where it can produce an amount of thrombomodulin that is substantially greater than an amount of thrombomodulin observed from a control medical device. An amount of thrombomodulin is "substantially greater" when the desired anti-thrombus effect is statistically improved over that observed from a control medical device. In some embodiments, a functional endothelium exists, or has been promoted, where the desired effects of thrombus inhibition, restenosis inhibition, and/or blood flow improvement from the presence of thrombomodulin becomes statistically observable when compared to a control development of such endothelium formation observed following implantation of a metal or polymer drug-eluting medical device that does not delay the onset of drug-elution for at least 5, 10, 12, 14, 15, 20, 25, 30, 45, 60, 75, or 90 days, or any range therein.

In addition, the coating may at least substantially inhibit development of a hyperproliferative tissue when compared to a control development of such hyperproliferative tissue observed following implantation of a metal or polymer medical device that does not elute a drug. One of skill will appreciate, for example, that hyperproliferative tissue growth includes a growth of tissue beyond what is normal and healthy. It can cause adverse effects on the function or physiology of the subject. On implants, fibrosis can build up and cause a stiffening of the tissue matrix surrounding the implant, limiting motion or healthy normal tissue compliance. In a blood vessel, hyperproliferation around the stent can cause a narrowing of the lumen and compromise blood flow. In some embodiments, the medical device comprises a stent.

The inhibition of the development of a hyperproliferative tissue can occur, or be promoted, when the amount of such tissue is in a quantity sufficient to show a statistical difference in an amount of tissue formation when compared to a control development of such an tissue, or lack thereof, observed following implantation of a control metal or polymer medical device that does not elute a drug. In some embodiments, the amount of hyperproliferative tissue produced from the control device is substantially greater than an amount of tissue observed from a medical device having a coating taught herein. An amount of tissue can be considered "substantially greater" when the measured amount is statistically greater. In some embodiments, restenosis is inhibited by at least 5, 10, 12, 14, 15, 20, 25, 30, 45, 60, 75, 90, 95, 99, 100 percent, or any amount therein, when compared to a control development of such restenosis formation observed following implantation of a metal or polymer medical device that does not elute a drug.

The coatings can be designed for a predetermined delay time and release rate of the drug. As described above, layers and sub-layers of coatings can be designed to have a different composition to impart more control over drug elution, coating hydrolysis, coating strength and integrity, other physical traits, and other such coating characteristics known to one of skill. In some embodiments, for example, the drug-reservoir layer can further comprise an accelerant layer to accelerate the time to onset of drug elution. In fact, in some embodiments, the accelerant layer can have a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons.

And, as described above, other variables, such as layer or sub-layer thickness, and/or thickness ratios between layers and/or sub-layers, can be used to obtain a desired delay time for drug release, release rate of the drug, fluid uptake in the coating, as well as coating strength, integrity, and the like. In some embodiments, the thickness of the coating can range from about 2 microns to about 9 microns, from about 1 micron to about 40 microns, from about 1 micron to about 30 microns, from about 2 microns to about 38 microns, from about 3 microns to about 36 microns, from about 4 microns to about 34 microns, from about 5 microns to about 7 microns, from about 4 microns to about 6 microns, or any range therein. In some embodiments, the thickness of the coating is less than 12 microns, less than 11 microns, less than 9 microns, less than 8 microns, less than 7 microns, less than 6 microns, less than 5 microns, or any range therein, such as, for example, from 7 microns to 12 microns, 9 microns to 12 microns, or 7 microns to 9 microns. In some embodiments, each layer or sub-layer can range from about 0.1 micron to about 10 microns, from about 0.1 micron to about 7 microns, from about 0.1 micron to about 5 microns, from about 0.1 micron to 3 microns, from about 0.1 micron to about 2 microns, from about 0.1 micron to about 0.9 microns, from about 0.1 micron to about 0.8 microns, from about 0.1 micron to about 0.7 microns, from about 0.1 micron to about 0.6 microns, from about 0.1 micron to about 0.5 microns, from about 0.1 micron to about 0.4 microns, from about 0.1 micron to about 0.3 microns, from about 0.3 micron to about 0.8 microns, from about 0.2 microns to about 5 microns, from about 0.2 microns to about 4 microns, from about 0.3 microns to about 3 microns, from about 0.5 microns to about 5 microns, from about 0.6 microns to about 3 microns from about 1 micron to about 3 microns, or any range therein.

In some embodiments, for example, the thickness ratio of the drug-reservoir layer to the drug-containing layer can range from about 4:1 to about 10:1, from about 4:1 to about 7:1, from about 2:1 to about 12:1, from about 3:1 to about 11:1, from about 5:1 to about 10:1, from about 2:1 to about 8:1, from about 4:1 to about 6:1, or any range therein. In some embodiments, the ratio can be a mass ratio, where the mass of the drug-reservoir layer to the mass of the drug-containing layer can range from 3:1 to 20:1, from 4:1 to 16:1, from 5:1 to 15:1, from 6:1 to 10:1, or any range therein.

In some embodiments thinner coatings and desired ratios can be achieved using higher percentages of drug in the drug-containing layer, where in some embodiments, the drug-containing layer is composed of 100, 99, 98, 97, 96, 95, 94, 93, 92, 91, 90 percent drug, or any range therein. The drug-containing layer can range from about 0.05 to about 5 microns, from about 0.03 to about 3 microns, from about 0.1 to about 2 microns, or any range therein in thickness, in some embodiments.

The relative hydrophobicity or hydrophilicity can also impart desired drug retention and elution behavior from the coating. For example, the miscibility of the drug in a coating can be preselected to affect the rate of drug migration in the coating, and/or elution from the coating. In some embodiments, the drug can be selected to be miscible in a coating to increase retention time in the coating. Likewise, in some embodiments, the drug can be selected to be less miscible, or immiscible, in a coating to decrease retention time in the coating.

As such, the teachings are generally directed to a method of inhibiting the formation of hyperproliferative tissue and promoting the formation of a functional endothelium after implantation of a medical device in a subject. The method can comprise applying a therapeutic coating on a medical device and implanting the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of implantation in the subject and functioning to retain and at least substantially block an initial release of the drug into the subject for a time sufficient to form a functional endothelium over the surface of the medical device, the functional endothelium providing a source of thrombomodulin to the subject.

Forming a Coating

One of skill will appreciate that a coating can be applied using any one, or any combination, of methods known in the art, where the terms "form" and "apply" can be used interchangeably, in some embodiments. The compositions can be in the form of coatings for medical devices such as, for example, a balloon-expandable stent or a self-expanding stent. There are many coating configurations possible, and each configuration can include any number and combination of layers. In some embodiments, the coatings can comprise one or a combination of the following four types of layers: (a) an agent layer, which may comprise a polymer and an agent or, alternatively, a polymer free agent; (b) an optional primer layer, which may improve adhesion of subsequent layers on the implantable substrate or on a previously formed layer; (c) an optional topcoat layer, which may serve as a way of controlling the rate of release of an agent; and (d) an optional biocompatible finishing layer, which may improve the biocompatibility of the coating.

In some embodiments, any one or any combination of layers can be used. And, each layer can be applied to an implantable substrate, for example, by any method including, but not limited to, dipping, spraying, pouring, brushing, spin-coating, roller coating, meniscus coating, powder coating, inkjet-type application or a combination thereof. In one example, each of the layers can be formed on a stent by dissolving one or more biodegradable polymers, optionally with a non-biodegradable polymer, in one or more solvents and either (i) spraying the solution on the stent or (ii) dipping the stent in the solution. In this example, a dry coating of biodegradable polymer may be formed on the stent when the solvent evaporates.

The formation of each layer may involve use of a casting solvent. A casting solvent is a liquid medium within which a polymer can be solubilized to form a solution that may be applied as a coating on a substrate. The casting solvent must be selected to avoid adversely affecting an underlying material such as, for example, an underlying primer layer or a bare stent structure. In one example, a material used to form the primer layer is soluble in a highly polar casting solvent but is reasonably insoluble in a low polarity casting solvent. A material is "reasonably insoluble" in a solvent when the material does not solubilize to an extent great enough to significantly affect the performance of the resulting product, meaning that the product can still be used for its intended purpose. In this example, an overlying agent layer that is soluble in a low polarity casting solvent can be applied to the underlying primer layer without disrupting the structure of primer layer.

The casting solvent may be chosen based on several criteria including, for example, its polarity, ability to hydrogen bond, molecular size, volatility, biocompatibility, reactivity and purity. Other physical characteristics of the casting solvent may also be taken into account including the solubility limit of the polymer in the casting solvent, the presence of oxygen and other gases in the casting solvent, the viscosity and vapor pressure of the combined casting solvent and polymer, the ability of the casting solvent to diffuse through an underlying material, and the thermal stability of the casting solvent.

One of skill in the art has access to scientific literature and data regarding the solubility of a wide variety of polymers. Furthermore, one of skill in the art will appreciate that the choice of casting solvent may begin empirically by calculating the Gibb's free energy of dissolution using available thermodynamic data. Such calculations allow for a preliminary selection of potential solvents to test in a laboratory. It is recognized that process conditions can affect the chemical structure of the underlying materials and, thus, affect their solubility in a casting solvent. It is also recognized that the kinetics of dissolution are a factor to consider when selecting a casting solvent, because a slow dissolution of an underlying material, for example, may not affect the performance characteristics of a product where the product is produced relatively quickly.

Casting solvents for use in the present invention include, but are not limited to, DMAC, DMF, THF, cyclohexanone, xylene, toluene, acetone, i-propanol, methyl ethyl ketone, propylene glycol monomethyl ether, methyl butyl ketone, ethyl acetate, n-butyl acetate, and dioxane. Solvent mixtures can be used as well. Examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:

50 w/w); acetone, xylene and FLUX REMOVER AMS (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, InC) (10:40:50 w/w); and 1,1,2-trichloroethane and chloroform (80:20 w/w).

It should be appreciated that a process of forming a medical article or coating can include additional process steps such as, for example, the use of energy such as heat, electromagnetic radiation, electron beam, ion or charged particle beam, neutral-atom beam, and chemical energy. The process of drying can be accelerated by using higher temperatures.

A medical article or coating can also be annealed to enhance the mechanical properties of the composition. Annealing can be used to help reduce part stress and can provide an extra measure of safety in applications such as complex medical devices, where stress-cracking failures can be critical. The annealing can occur at a temperature that ranges from about 30 degrees C. to about 200 degrees C., from about 35 degrees C. to about 190 degrees C., from about 40 degrees C. to about 180 degrees C., from about 45 degrees C. to about 175 degrees C., or any range therein. The annealing time can range from about 1 second to about 60 seconds, from about 1 minute to about 60 minutes, from about 2 minute to about 45 minutes, from about 3 minute to about 30 minutes, from about 5 minute to about 20 minutes, or any range therein. The annealing can also occur by cycling heating with cooling, wherein the total time taken for heating and cooling is the annealing cycle time.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. The amount of mobilization of the drug can be considered "substantially inhibited" when the measured amount of mobilization of the drug from the drug-containing layer is statistically less than if the drying procedure was not used as taught herein.

The application of the sub-layers can be used to at least substantially promote a retention of the drug in the drug-containing layer during formation of the coating when compared to such a coating without the application of the sub-layers. The amount of retention of the drug can be considered "substantially promoted" when the measured amount of retention of the drug from the drug-containing layer is statistically greater than if the sub-layer application as taught herein was not used.

In some embodiments, the drug-retaining layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-retaining layer, is more hydrophilic than the remainder of the drug-retaining layer, and comprises at least one sub-layer having a thickness of less than or equal to 3 microns, where a repeated application the sub-layer is used to form thicknesses of greater than 3 microns. The accelerant layer can contain some of the drug. In some embodiments, the drug composes less than 30, 25, 20, 15, 10, 7, 5, 4, 3, 2, 1 percent, or any amount therein, of the accelerant layer. And, in some embodiments the drug composes less than 10 percent of the accelerant layer.

The coatings can be heterogeneous in morphology. For example, a hydrophobic layer can contain hydrophilic regions. Likewise, a more hydrophilic coating can have hydrophobic regions. The hydrophilic regions can be in the form of isolated packages of material, or "islands" in some embodiments, where the isolated hydrophilic package can add to the water absorption rate, and thus hydrolysis rate, of the coating. The isolated packages may be added during the coating process as droplets, in some embodiments. The coatings taught herein can, in some embodiments, further comprise pockets of hydrophilic material in the drug-retaining layer, wherein the hydrophilic material can comprise a second drug. There can be one or more such pockets, and the pockets can be positioned anywhere throughout the coating. In some embodiments, one or more hydrophilic pockets are positioned in the drug reservoir layer and, in some embodiments, one or more hydrophilic pockets are positioned in the drug-retaining layer. In some embodiments, the hydrophilic pockets comprise a drug selected from the group consisting of dextran, heparin, ticlopidine, chlopidogrel, enoxaparin, dalteparin, hirudin, bivalirudin, argatroban, and danparoid.

A Method of Forming a Coating

The coating can be applied to a surface of a medical device using, for example, wet chemistry and acetone as a solvent with techniques known to one of skill. A bare metal stent can be coated with a drug-containing layer mixed in a volatile solvent. At least one drug and polymer is dissolved into the volatile solvent to form a drug solution, and the drug can be an anti-proliferative, such as rapamycin. The volatile solvent can be acetone, dichloromethane, or a mixture of the two solvents.

In one example, about 1-2 micron of a drug-containing layer can be covered with a 1-3 micron accelerant layer made of acid terminated 75/25 monomer ratio PLGA having a molecular weight of 90-120 KDalton, and the accelerant layer can be covered with about 6-12 microns of ester terminated 75/25 monomer ratio PLGA having a molecular weight of 100-160 KDalton. This unique and novel combination of compositions in different layers, as well as the relative thicknesses and positioning of the layers, can provide a coating having a desired delay in the onset of drug elution. The elution, in fact, can be delayed for a designed, prolonged period of time, at which time the drug release is fast enough to have a therapeutic effect. The coating is robust, maintaining functional integrity through stresses and strains of assembly and deployment. And, the coating can maintain a low enough profile of the implant for ease of delivery and introducing less foreign material into the body.

The following is an example of a process that can be used to create composite elution layers, a process comprising multiple sub-layer applications, such as those described herein. The drug is added to the solvent for wet chemistry application, and the drug-containing layer may be applied to the surface of the device. The drug-containing layer can be 120 nanometers and 6 microns, 200 nanometers and 3 microns, 0.7-1.1 microns, or any range therein, thick in some embodiments. The drug-containing layer is then dried with convection of a non reactive gas, such as nitrogen, at a temperature elevated above room temperature.

The accelerant layer polymer is mixed with a solvent for wet chemistry application, and the accelerant layer is created by layering multiple sub-layers of the same material. Each sub-layer is coated onto previous layer and dried with convection of gas as described in above using a drying time of about 1-2 hours before coating the next sub-layer/layer. The accelerant layer can be about 1-2 microns thick and composed of 50:50 PLGA with acid terminal end-groups. In some embodiments, the accelerant layer can be about 3-5 microns thick and composed of 2-3 sub-layers of 75:25 PLGA with acid terminal end-groups. And, in some embodiments, the accelerant layer can be between about 120 nanometers and 6 microns, 400 nanometers and 4 microns, 500 nanometers and 5 microns, or any range therein. Moreover, the concentration of the drug in the accelerant layer can be less than 50% of the drug-containing layer before implantation in some embodiments.

The drug-retaining layer can then be prepared and coated onto the accelerant layer and dried. The drug-retaining layer is applied by layering multiple sub-layers of the same material. Each sub-layer is coated onto previous layer and dried using convection of gas as described above with drying times of about 1-2 hours before coating the next sub-layer/layer. The drug-retaining layer can be about 3-5 times the thickness of the accelerant layer, in some embodiments, if the accelerant layer is composed of 50:50 PLGA having an ester terminal end-group in some embodiments. In some embodiments, the thickness of the drug-retaining layer can be about 0.2-2 times that of the accelerant layer, if the accelerant layer is composed of 75:25 PLGA having an ester terminal end-group. The entire assembly may then be packaged and sterilized for deployment.

One of skill will appreciate that any non-reactive or substantially non-reactive gas can be used including, but not limited to, nitrogen, carbon dioxide, or a noble gas. The heated gas's temperature can be, for example, between about 70 degrees F. and the drug's melting point. In some embodiments, the gas's temperature can be between about 70 degrees F. and 240 degrees F., from 140-190 degrees F., or any range therein. The specified drying time can be, for example, between about 0 minutes and 3 hours, 10-30 minutes, 30 minutes and 1 hour, 15 minutes and 2 hours, or any range therein. The gas surface flow rate can be between about 40 and 500 inches per second, 50 and 400 inches per second, 100 and 500 inches per second, or any range therein. In some embodiments, the gas surface flow rate is 90-150 inches/seC The Drugs or Agents It should be appreciated that, in some embodiments, the term "agent" or "drug" can be used interchangeably. An "agent" or "drug" can be a moiety, for example, that may be bioactive, biobeneficial, diagnostic, plasticizing, or have a combination of these characteristics. A "moiety" can be a functional group composed of at least 1 atom, a bonded residue in a macromolecule, an individual unit in a copolymer or an entire polymeric block. It is to be appreciated that any medical articles that can be improved through the teachings described herein are within the scope of the present invention. Examples of medical devices include, but are not limited to, stents, stent-grafts, vascular grafts, artificial heart valves, foramen ovale closure devices, cerebrospinal fluid shunts, pacemaker electrodes, guidewires, ventricular assist devices, cardiopulmonary bypass circuits, blood oxygenators, coronary shunts, and endocardial leads.

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

In one example, a biological benefit may be that the polymer or coating becomes non-thrombogenic, such that protein absorption is inhibited or prevented to avoid formation of a thromboembolism; promotes healing, such that endothelialization within a blood vessel is not exuberant but rather forms a healthy and functional endothelial layer; or is non-inflammatory, such that the biobeneficial agent acts as a biomimic to passively avoid attracting monocytes and neutrophils, which could lead to an event or cascade of events that create inflammation.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of biobeneficial agents include, but are not limited to, many of the polymers listed above such as, for example, carboxymethylcellulose; poly(alkylene glycols) such as, for example, PEG; poly(N-vinyl pyrrolidone); poly(acrylamide methyl propane sulfonic acid); poly(styrene sulfonate); sulfonated polysaccharides such as, for example, sulfonated dextran; sulfated polysaccharides such as, for example, sulfated dextran and dermatan sulfate; and glycosaminoglycans such as, for example, hyaluronic acid and heparin; and any derivatives, analogs, homologues, congeners, salts, copolymers and combinations thereof. In some embodiments, the biobeneficial agents can be prohealing such as, for example, poly(ester amides), elastin, silk-elastin, collagen, atrial natriuretic peptide (ANP); and peptide sequences such as, for example, those comprising Arg-Gly-Asp (RGD). In other embodiments, the biobeneficial agents can be non-thrombotics such as, for example, thrombomodulin; and antimicrobials such as, for example, the organosilanes. It is to be appreciated that one skilled in the art should recognize that some of the groups, subgroups, and individual biobeneficial agents may not be used in some embodiments of the present invention.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the teachings herein include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin $I_1$, actinomycin $X_1$, actinomycin $C_1$, and dactinomycin (COSMEGEN, Merck & Co., InC). Antineoplastics or antimitotics include, for example, paclitaxel (TAXOL, Bristol-Myers Squibb Co.), docetaxel (TAXOTERE, Aventis S.A.), methotrexate, azathioprine, vincristine, vinblastine, fluorouracil, doxorubicin hydrochloride (ADRIAMYCIN, Pfizer, InC) and mitomycin (MUTAMYCIN, Bristol-Myers Squibb Co.), and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethyl ketone (synthetic antithrombin), dipyridamole, glycoprotein IIb/IIIa platelet membrane receptor antagonist antibody, recombinant hirudin, and thrombin inhibitors (ANGIOMAX, Biogen, InC), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN and CAPOZIDE, Bristol-Myers Squibb Co.), cilazapril or lisinopril (PRINIVIL and PRINZIDE, Merck & Co., InC); calcium channel blockers such as nifedipine; colchicines; fibroblast growth factor (FGF) antagonists, fish oil (omega 3-fatty acid); histamine antagonists; lovastatin (MEVACOR, Merck & Co., InC); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST, Santen, InC), and any prodrugs, metabolites, analogs, homologues, congeners, derivatives, salts and combinations thereof.

Other bioactive agents useful in the teachings herein include, but are not limited to, free radical scavengers; nitric oxide donors; rapamycin; methyl rapamycin; 42-Epi-(tetrazoylyl) rapamycin (ABT-578); everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs; estradiol; clobetasol; idoxifen; tazarotene; alpha-interferon; host cells such as epithelial cells; genetically engineered epithelial cells; dexamethasone; and any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (4-hydroxy-TEMPO), 2,2',3,4,5,5'-hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

The drugs eluted from the coatings taught herein can function as an anti-proliferative or immunosuppressant. In some embodiments, the drug can be rapamycin or a derivative of rapamycin. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, and estradiol. One of skill will appreciate that agents that affect vascular smooth muscle cell (VSMC) proliferation or migration can also be used in some embodiments, including, but not limited to transcription factor E2F1.

The agents of the present invention can be used alone or in combination with other agents to obtain other desired functions of the polymeric compositions. The amounts of the agents that compose the polymeric compositions vary according to a variety of factors including, but not limited to, the biological activity of the agent; the age, body weight, response, or the past medical history of the subject; the type of atherosclerotic disease; the presence of systemic diseases such as, for example, diabetes; the pharmacokinetic and pharmacodynamic effects of the agents or combination of agents; and the design of the compositions for sustained release of the agents. Factors such as these are routinely considered by one of skill in the art when administering an agent to a subject in a desired amount to obtain a desired effect. In some embodiments, the desired amount is termed an "effective amount," where the amount administered elicits a desired response. In some embodiments, the effective amount can be a "therapeutically effective amount", administered in an amount that prevents, inhibits, or ameliorates the symptoms of a disease.

It is to be appreciated that the design of a composition for drug release can be dependent on a variety of factors such as, for example, the therapeutic, prophylactic, ameliorative or diagnostic needs of a patient or condition. In some embodiments, the agent can comprise an antiproliferative and should have a sustained release ranging from about 1 week to about 10 weeks, from about 2 weeks to about 8 weeks, from about 3 weeks to about 7 weeks, from about 4 weeks to about 6 weeks, and any range therein. In some embodiments, the agent can comprise an anti-inflammatory and should have a sustained release ranging from about 6 hours to about 3 weeks, from about 12 hours to about 2 weeks, from about 18 hours to about 10 days, from about 1 day to about 7 days, from about 2 days to about 6 days, or any range therein. In general, the sustained release should range from about 4 hours to about 12 weeks; alternatively, from about 6 hours to about 10 weeks; or from about 1 day to about 8 weeks.

Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and any range therein, where the percentage is based on the total weight of the polymer and agent or combination of agents.

The medical devices discussed herein can be any devices known to one of skill to benefit from the teachings provided. A medical device, for example, can be comprised of a metal or an alloy, including, but not limited to, ELASTINITE, NITINOL, stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY, Elgiloy Specialty Metals, InC; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that, are comprised of bioabsorbable polymers or biostable polymers are also included within the scope of the present invention.

Optional Plasticizers

The terms "plasticizer" and "plasticizing agent" can be used interchangeably in the teachings herein, and refer to any agent, including any agent described above, where the agent can be added to a polymeric composition to modify the mechanical properties of the composition or a product formed from the composition. Plasticizers can be added, for example, to reduce crystallinity, lower the glass-transition temperature (Tg), or reduce the intermolecular forces between polymers, with design goals that may include, but are not limited to, enhancing mobility between polymer chains in the composition. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading. Toughness can be measured using Charpy and Izod impact tests to assess the brittleness of a material.

A plasticizer can be monomeric, polymeric, co-polymeric, or a combination thereof, and can be combined with a polymeric composition in the same manner as described above for the biobeneficial and bioactive agents. Plasticization and solubility are analogous in the sense that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers such as single-block polymers, multi-block polymers, and copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly (esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly (alkylene glycols) such as poly(ethylene glycols) (PEG), poly (propylene glycols), and poly(ethylene/propylene glycols); low molecular weight poly(ethylene glycols) such as, for example, PEG 400 and PEG 6000; PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide and dimethyl formamide; sulfoxides such as for example, dimethyl sulfoxide; pyrrolidones such as, for example, n-methylpyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other embodiments, the plasticizers can be vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid. In other embodiments, the plasticizers can be essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli oil, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and any analogs, derivatives, copolymers and combinations thereof.

The molecular weights of the plasticizers can vary. In some embodiments, the molecular weights of the plasticizers range from about 10 Daltons to about 50,000 Daltons; from about 25 Daltons to about 25,000 Daltons; from about 50 Daltons to about 10,000 Daltons; from about 100 Daltons to about 5,000 Daltons; from about 200 Daltons to about 2500 Daltons; from about 400 Daltons to about 1250 Daltons; and any range therein. In other embodiments, the molecular weights of the plasticizers range from about 400 Daltons to about 4000 Daltons; from about 300 Daltons to about 3000 Daltons; from about 200 Daltons to about 2000 Daltons; from about 100 Daltons to about 1000 Daltons; from about 50 Daltons to about 5000 Daltons; and any range therein. The molecular weights are taught herein as a number average molecular weight.

The amount of plasticizer used in the teachings herein, can range from about 0.001% to about 70%; from about 0.01% to about 60%; from about 0.1% to about 50%; from about 0.1% to about 40%; from about 0.1% to about 30%; from about 0.1% to about 25%; from about 0.1% to about 20%; from about 0.1% to about 10%; from about 0.4% to about 40%; from about 0.6% to about 30%; from about 0.75% to about 25%; from about 1.0% to about 20%; and any range therein, as a weight percentage based on the total weight of the polymer and agent or combination of agents.

It should be appreciated that any one or any combination of the plasticizers described above can be used in the teachings herein. For example, the plasticizers can be combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

Various Applications

In some embodiments, the drug-containing layer may be applied to a surface of a prosthesis, and the drug-reservoir layer may be applied on or over the drug layer. The prosthesis can comprise a stent, such as a bare metal stent, or a stent delivery system. In some embodiments, the prosthesis can comprise a fitting for mechanically coupling to an adjacent tissue, such as calcified or soft tissue, for example, a bone implant or intra-organ implant. In some embodiments, the system may comprise an entirely resorbable construct, such as a capsule, a tablet, a pellet, a shaft, a rod, a sphere, disc, or a ring. In some embodiments, the resorbable construct may be configured for deployment in an anatomic environment such as the gastrointestinal tract, a synovial joint, a cardiovascular lumen, a cardiovascular chamber, a urinary lumen, a urinary chamber, a reproductive lumen, a reproductive chamber, a gynecological lumen, a gynecological chamber, an endocrine lumen, or an endocrine chamber.

In one example, a tubular drain system can be implanted, leading from one of the ventricles of the brain to an abdominal position. One or more portions, or all, or the drain system may be coated and configured to promote endothelization/healing by substantially blocking elution of antiproliferative drugs, before controllably eluting drugs to prevent excessive fibrous cellular encapsulation and/or stenosis.

In another example, portions of a "venous" needle or "arterial" needle in an arteriovenous fistula may be coated and configured to promote endothelization/healing by substantially blocking elution of antiproliferative drugs, before controllably eluting drugs to prevent stenosis and/or excessive cellular encapsulation. Many transcutaneous port or cannulation device configurations may be so treated.

In another example, portions of pacemaker, defibrillator, or other implantable device leads, such as a distal portion configured to engage a portion of the endocardial wall, may be coated and configured to promote endothelization/healing by substantially blocking elution of antiproliferative drugs, before controllably eluting drugs to prevent excessive cellular encapsulation.

In another example, portions of an intraocular lens prosthesis, such as the main body or legs of the prosthesis may be coated and configured to promote endothelization/healing by substantially blocking elution of antiproliferative drugs, before controllably eluting drugs to prevent excessive cellular encapsulation.

In another example, portions of a bile duct or other duct, tube, vessel, or lumen prosthesis may be coated and configured to promote endothelization/healing by substantially blocking elution of antiproliferative drugs, before controllably eluting drugs to prevent stenosis and/or excessive cellular encapsulation.

In another example, portions of a breast prosthesis, or prostheses for other applications, may be coated and configured to promote endothelization/healing by substantially blocking elution of antiproliferative drugs, before controllably eluting drugs to prevent excessive cellular encapsulation and/or adhesion.

In another example, pellets or small prostheses used to treat tissue volumes such as those of a prostate gland may be coated and configured to promote endothelization/healing by substantially blocking elution of antiproliferative drugs, before controllably eluting drugs.

In another example, immunosuppressants and/or cytotoxics, such as taxol, can be delivered in such devices to aid in the treatment of tumors, such as prostate or other tumors. Pellets containing such drugs, for example, may be delivered through the urethra or by other surgical means.

In another example, severed nerve portions may be joined with a graft comprising an outer sheath of coated drug eluting material configured to protect and isolate the inner graft material while also promoting endothelization/healing by substantially blocking elution of antiproliferative drugs, before controllably eluting drugs to discourage excessive cellular overgrowth which may lead to nerve impingement and/or adhesion.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

EXAMPLE 1

Creating a First Therapeutic Coating Having a Programmed Delayed Time Before the Onset of Drug Release This example teaches one way to create a therapeutic coating on a medical device, where the coating has a drug-containing layer, a drug-retaining layer, and an accelerant layer, and the coating provides a programmed delayed time before the onset of drug release.

The Design

The drug-containing layer has 81% (w/w) rapamycin in 75:25 PLGA, a MW of 100 KDaltons, is carboxylic acid terminated, 1 micron thickness. The accelerant layer has pure 75:25 PLGA, 100 KDaltons, carboxylic acid terminated, 5 micron; and, Drug Retaining Layer: Pure 75:25 PLGA, 120 KDaltons, ester (methoxy) terminated, and 2 micron thickness The Manufacturing Method Rapamycin and poly(lactic-co-glycolic acid) (PLGA) are weighed in an 81% mass Rapamycin and 19% mass PLGA, and dissolved in acetone to yield a 1% mass per volume drug coating solution. The specific PLGA used is 75% lactide and 25% glycolide, carboxylic acid end groups, and a molecular weight of 100,000 Daltons.

The drug coating solution is deposited onto a bare metal stent using a high precision vibratory sprayer, MEDICOAT manufactured by SonoTek Corporation of Milton, N.Y. to produce the drug-containing layer which is approximately 1 micron in thickness.

After the drug-containing layer is deposited, the residual volatile acetone is removed by flowing nitrogen gas heated to 160 degrees Fahrenheit over the surface of the drug-containing layer 20 minutes. The velocity of the heated nitrogen passing over the coating is between 70 and 100 inches per second. Mid-way through the specified drying time, the stent is rotated 180 degrees. The nitrogen is heated by a hot box and the nitrogen is fed into the hot box from a nitrogen tank.

PLGA with 75% lactide and 25% glycolide, carboxylic acid end groups, and a molecular weight of 100,000 Daltons is dissolved in acetone to a 1% mass per volume accelerant coating solution.

The accelerant coating solution is applied on top of the drug-containing layer using a high precision vibratory sprayer, MEDICOAT manufactured by SonoTek Corporation of Milton, N.Y. to create the first accelerant layer which is 2 microns thick.

After the first accelerant layer is deposited, the residual volatile acetone is removed by flowing nitrogen gas heated to 160 degrees Fahrenheit over the surface of the drug-containing layer 40 minutes. The velocity of the heated nitrogen passing over the coating is between 70 and 100 inches per second. Mid-way through the specified drying time, the stents are rotated 180 degrees. The nitrogen is heated by a hot box and the nitrogen is fed into the hot box from a nitrogen tank.

PLGA with 75% lactide and 25% glycolide, carboxylic acid end groups, and a molecular weight of 100,000 Daltons is dissolved in acetone to a 1% mass per volume accelerant coating solution.

The accelerant coating solution is applied on top of the first accelerant layer using a high precision vibratory sprayer, MEDICOAT manufactured by SonoTek Corporation of Milton, N.Y. to create the second accelerant layer which is 3 microns thick.

After the second accelerant layer is deposited, the residual volatile acetone is removed by flowing nitrogen gas heated to 160 degrees Fahrenheit over the surface of the drug-containing layer 40 minutes. The velocity of the heated nitrogen passing over the coating is between 70 and 100 inches per second. Mid-way through the specified drying time, the stents are rotated 180 degrees. The nitrogen is heated by a hot box and the nitrogen is fed into the hot box from a nitrogen tank.

PLGA with 75% lactide and 25% glycolide, ester end groups, and a molecular weight of 120,000 Daltons is dissolved in acetone to a 1% mass per volume drug retaining coating solution.

The drug-retaining coating solution is applied on top of the second accelerant layer using a high precision vibratory sprayer, MEDICOAT manufactured by SonoTek Corporation of Milton, N.Y. to create the drug retaining layer which is 2 microns thick.

After the drug-retaining layer is deposited, the residual volatile acetone is removed by flowing nitrogen gas heated to 160 degrees Fahrenheit over the surface of the drug-containing layer 40 minutes. The velocity of the heated nitrogen passing over the coating is between 70 and 100 inches per second. Mid-way through the specified drying time, the stents are rotated 180 degrees. The nitrogen is heated by a hot box and the nitrogen is fed into the hot box from a nitrogen tank.

EXAMPLE 2

Creating a Second Therapeutic Coating Having a Programmed Delayed Time Before the Onset of Drug Release This example teaches one way to create a therapeutic coating on a medical device, where the coating has a drug-containing layer, a drug-retaining layer, and an accelerant layer, and the coating provides a programmed release of a drug.

The Design

The drug-containing layer has 20% (w/w) rapamycin in 75:25 PLGA, a MW of 140 KDaltons, is carboxylic acid terminated, 6 microns thick. The accelerant layer has pure 75:25 PLGA, 100 KDaltons, carboxylic acid terminated, 6 microns thick; and, Drug Retaining Layer: Pure 75:25 PLGA, 120 KDaltons, ester (methoxy) terminated, 12 microns thick.

The Manufacturing Method

Rapamycin and poly(lactic-co-glycolic acid) (PLGA) are weighed in an 20% mass Rapamycin and 80% mass PLGA, and dissolved in acetone to yield a 1% mass per volume drug coating solution. The specific PLGA used is 75% lactide and 25% glycolide, has ester end groups, and has a molecular weight of 140,000 Daltons.

The drug coating solution is deposited onto a bare metal stent using a high precision vibratory sprayer, MEDICOAT manufactured by SonoTek Corporation of Milton, N.Y. to produce the drug-containing layer which is approximately 6 microns in thickness. After the drug-containing layer is deposited, the residual volatile acetone is removed by flowing nitrogen gas over the surface of the drug-containing layer for 3 hours.

PLGA with 75% lactide and 25% glycolide, having carboxylic acid end groups and a molecular weight of 100,000 Daltons, is dissolved in acetone to a 1% mass per volume accelerant coating solution.

The accelerant layer coating solution is applied on top of the drug-containing layer using a high precision vibratory sprayer, MEDICOAT manufactured by SonoTek Corporation of Milton, N.Y. to create the accelerant layer which is 6 microns thick. After the accelerant layer is deposited, the residual volatile acetone is removed by flowing nitrogen gas for 3 hours.

PLGA with 75% lactide and 25% glycolide, having ester end groups and a molecular weight of 140,000 Daltons, is dissolved in acetone to a 1% mass per volume drug retaining coating solution.

The drug-retaining coating solution is applied on top of the accelerant layer using a high precision vibratory sprayer, MEDICOAT manufactured by SonoTek Corporation of Milton, N.Y. to create the first drug retaining layer which is 6 microns thick. After the first drug-retaining layer is deposited, the residual volatile acetone is removed by flowing nitrogen over the surface of the drug-containing layer 3 hours.

PLGA with 75% lactide and 25% glycolide, having ester end groups and a molecular weight of 140,000 Daltons, is dissolved in acetone to a 1% mass per volume drug retaining coating solution.

The drug retaining coating solution is applied on top of the first drug-retaining layer using a high precision vibratory sprayer, MEDICOAT manufactured by SonoTek Corporation of Milton, N.Y. to create the second drug-retaining layer which is 6 microns thick. After the second drug retaining layer is deposited, the residual volatile acetone is removed by flowing nitrogen over the surface of the drug-containing layer 3 hours.

EXAMPLE 3

A Programmed Coating can be Designed to Allow for a Particular Delay in Initial Release of a Drug and a Particular Release Rate This example shows that a delay time in an initial release of a drug can be programmed by coating design and can vary independent of the elution rate of the drug. By varying the coating composition within the parameters taught herein, for example, the coating of Example 1 was designed and produced to have a delay time of 26 days for an initial release of the drug from the drug-retaining layer.

Elution Medium

Preparing a 2% w/w Tween 20 solution in phosphate buffered saline solution:

Materials: Polysorbate 20 (Tween 20); phosphate buffered tablets; distilled water; gravimetric balance having a sensitivity to 4 or 5 decimal places; stir bar; stir plate; glass beaker; flask or a plastic container; disposable polyethylene transfer pipet; graduated measuring container.

Procedure

The glass or plastic container is placed on the balance. 4 g of Tween 20 is transferred to the container using a disposable polyethylene transfer pipet. 2 Phosphate buffered tablets are added to the container. 200 ml of distilled water is added to the container possessing Tween 20 and the phosphate buffered tablets. A stir bar is placed into the container, and the container is placed onto the stir plate and stirred until the Tween 20 and phosphate buffered tablets are completely dissolved. The stirring will take approximately 20 minutes. The medium can be used as needed and stored at room temperature for up to 7 days. If storing, cover the top with paraffin wax to minimize evaporation.

In Vitro Elution Test Method

Materials: 3.5 ml PTFE bottles; 5 ml pipette; 5 ml pipette tips; disposable polyethylene transfer pipet; 2% w/w Tween PBS solution (as prepared above); hybridization oven with carousel; quartz cuvette; spectrophotometer; rubber bands; KIMWIPES.

Procedure

Place each stent into a properly labeled 3.5 ml PTFE bottle. Using the 5 ml pipette and pipette tips fill the 3.5 ml PTFE bottles with 3.5 ml of 2% Tween PBS solution. Individually place each PTFE bottle on the carousel fixture in the oven and use rubber bands to affix the PTFE bottles to the carousel. Set the hybridization oven to 37° C. and the carousel speed to 20 rpm.

Medium change procedure: At the desired day to change the medium, remove the 3.5 ml PTFE bottles from the hybridization oven. Using a clean polyethylene transfer pipette, place the solution to be used as the blank into the quartz cuvette and blank the system. Use a clean polyethylene transfer pipette to remove the solution from the PTFE bottle and pipette into the quartz cuvette. Make sure no bubbles are present in the quartz cuvette solution. Using a KIMWIPE, remove any smudges, contaminants or liquid from the side of the quartz cuvette. Place the quartz cuvette into the spectrophotometer (the clear portion of the cuvette should be facing the light source). Initiate the spectrophotometer to read the absorbance values over the wavelength range of 220 nm to 500 nm. Observe for a rapamycin peak and record the absorbance value at 280 nm. Save the file in an appropriate folder. Remove the remaining solution from the 3.5 ml PTFE vial and pipette into rapamycin waste solution container. Remove the solution from the quartz cuvette and pipette into the rapamycin waste container. Wash the cuvette three times with distilled water to remove residual rapamycin in the cuvette and discard washing solution into the rapamycin waste container. Repeat medium change procedure for all samples.

After all bottles have been read and changed, fill the PTFE bottles with 3.5 ml of 2% Tween solution. Return all samples to the hybridization oven. Individually place each PTFE bottle on the carousel fixture in the oven and use rubber bands to affix the PTFE bottles to the carousel. Set the hybridization oven to 37° C. and the carousel speed to 20 rpm.

Figure 5A:
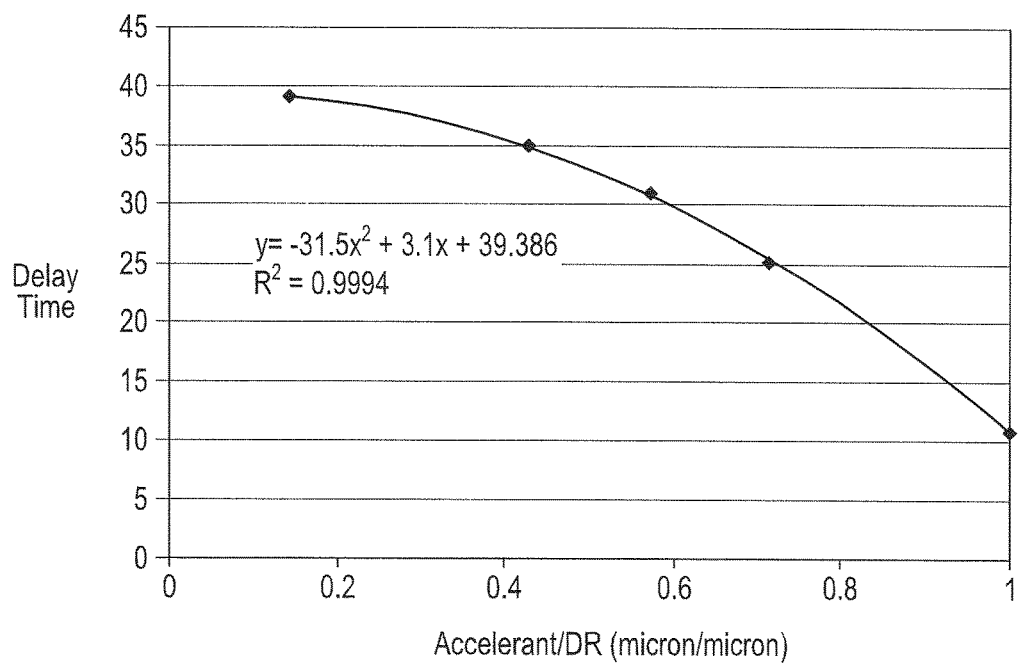
FIGS. 5A and 5B show the effects of varying coating design to obtain (ii) a desired delay time in an initial release of a drug and (ii) a desired elution rate, according to some embodiments.
Figure 5B:
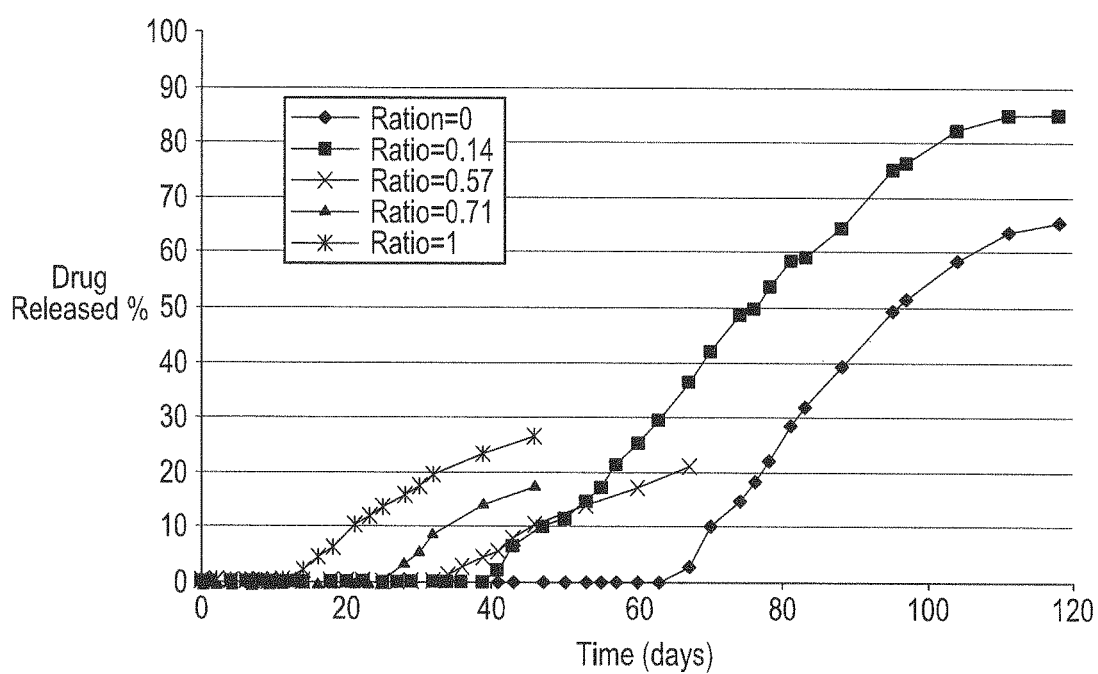

FIGS. 5A and 5B show the effects of varying coating design to obtain (ii) a desired delay time in an initial release of a drug and (ii) a desired elution rate, according to some embodiments. As shown in FIG. 5A, the delay time can be programmed to vary independent of the drug elution rate by varying the thickness ratio of the accelerant layer (Accelerant) to the drug-reservoir layer (DR). FIGS. 5A and 5B shows that as the Accelerant/DR ratio increases from 0 to 1, the delay time, delaying the onset of the initial release, decreases according to the following formula: $y=-31.5x^2+3.1x+38.375$ with an excellent correlation $R^2$ of 0.9994 for this particular combination of coating layers.

EXAMPLE 4

A Programmed Coating Allows for Development of a Functional Endothelium as Additional, Localized Source of Thrombomodulin This example shows that the coatings taught herein at least substantially promote development of the functional endothelium as an additional, localized source of thrombomodulin when compared to a control development of such endothelium formation observed following implantation of a metal or polymer drug-eluting stent.

Figure 6:
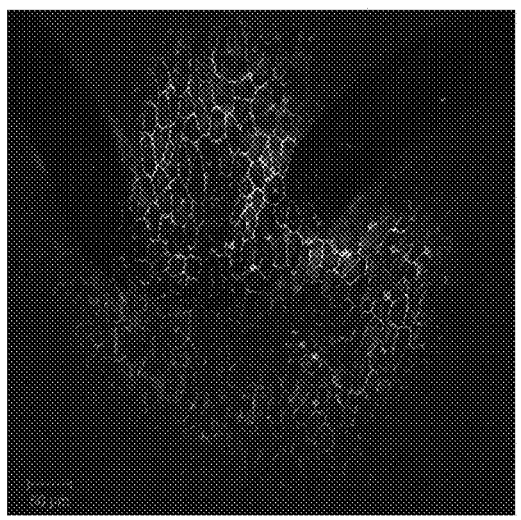
FIGS. 6A and 6B compare the relative amounts of thrombomodulin expressed from a rabbit iliac artery when using a popular drug-eluting stent and a stent having the programmed coatings taught herein, according to some embodiments.
Figure 6:
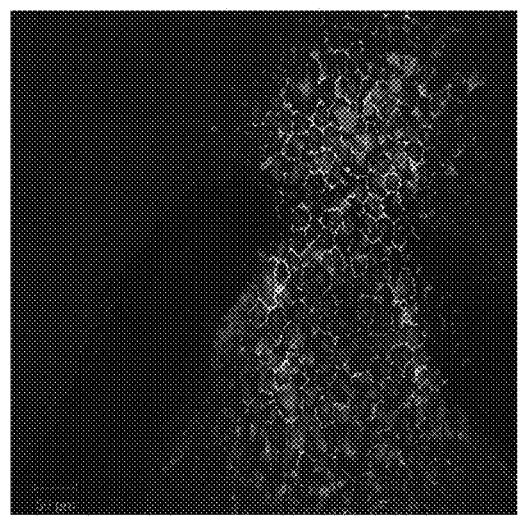

FIGS. 6A and 6B compare the relative amounts of thrombomodulin expressed from a rabbit iliac artery when using a popular drug-eluting stent and a stent having the programmed coatings taught herein, according to some embodiments. FIGS. 6A and 6B show differences in the degree of functional endothelialization between a stent coated as taught herein and the best of the marketed drug-eluting stents. Note the high prevalence of thrombomodulin expressed around the stent as taught herein as opposed to minimal prevalence of thrombomodulin on the competitor stent.

Figure 7:
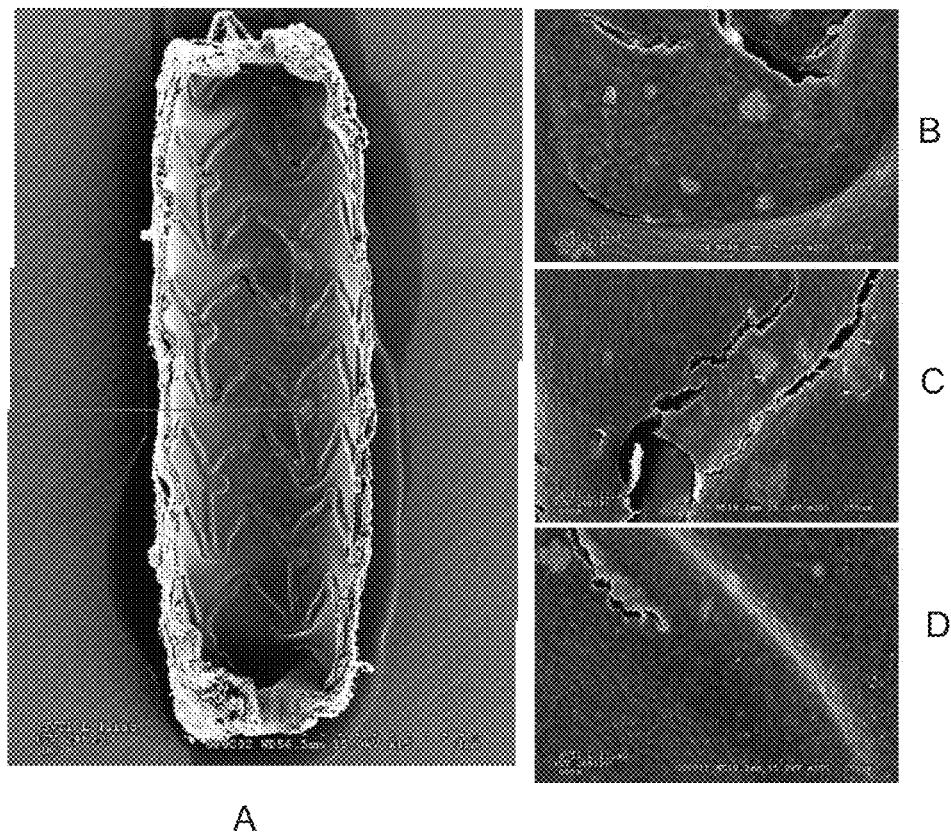
FIGS. 7A and 7B compare the relative amounts of endothelium that developed over stent struts in rabbit iliac arteries over a period of 2 weeks when using a popular drug-eluting stent and a stent having the programmed coatings taught herein, according to some embodiments.
Figure 7:
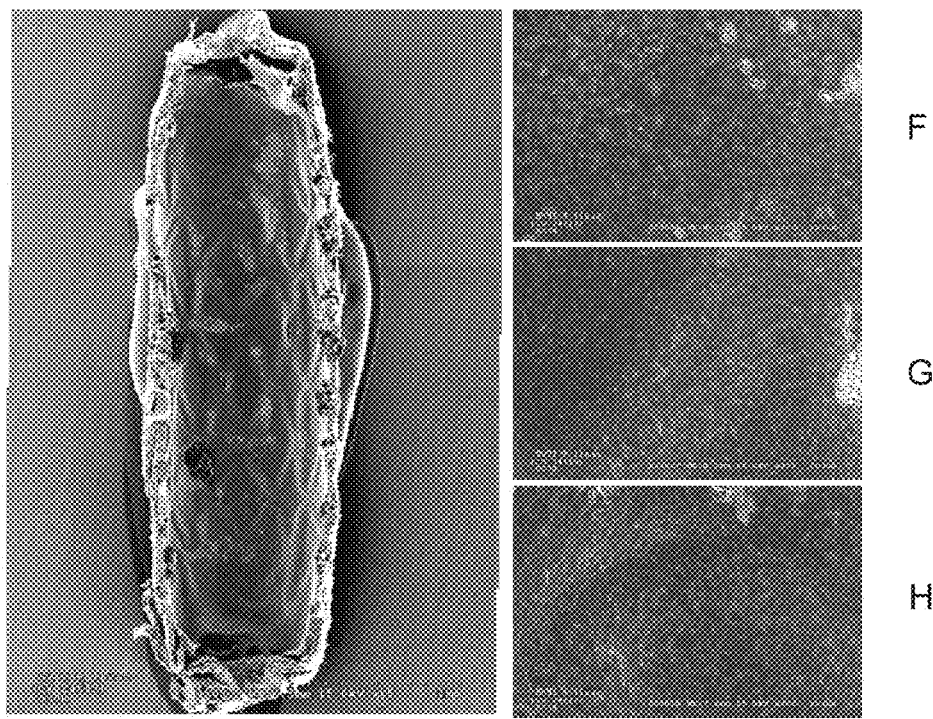
Figure 8:
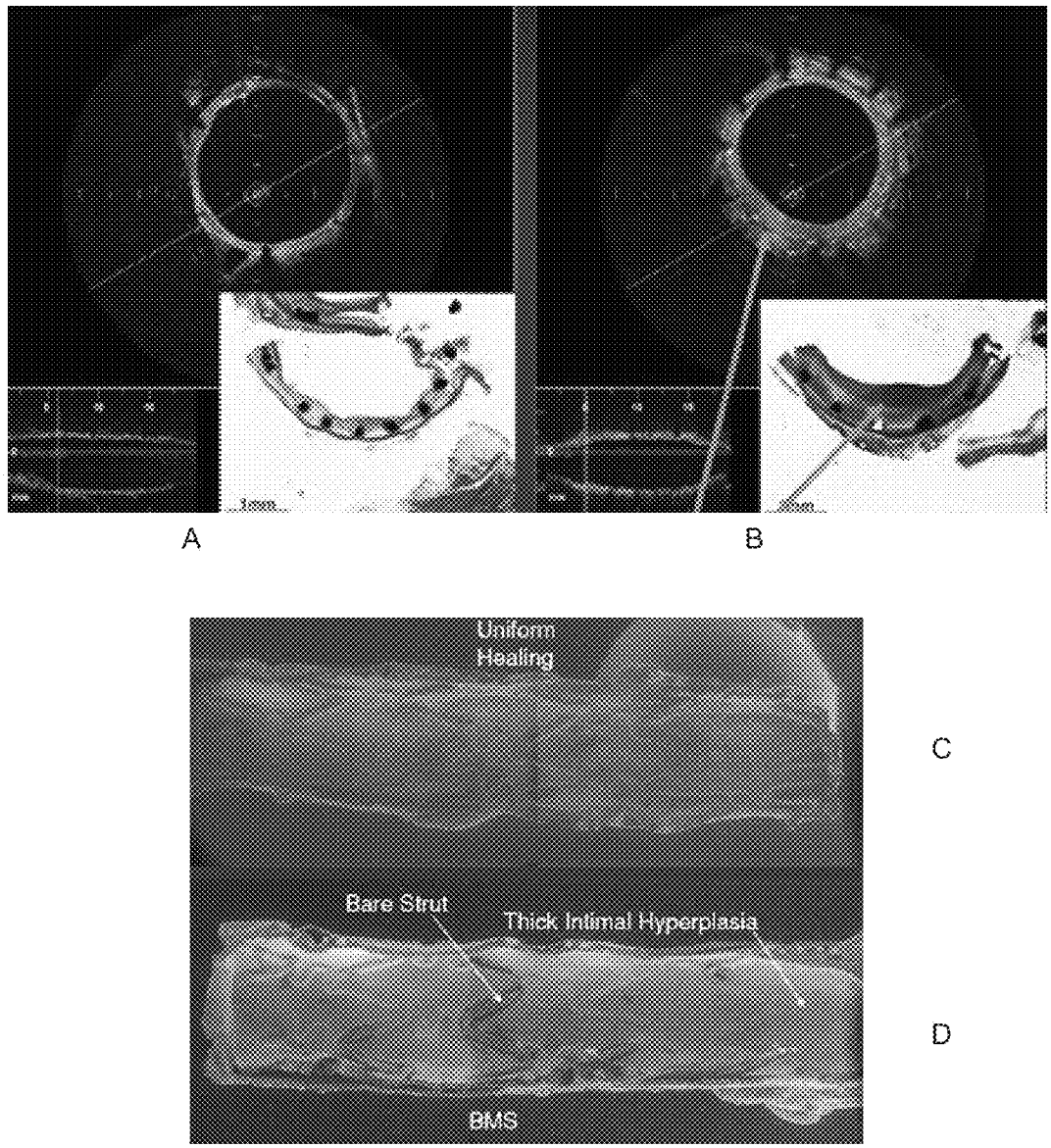
FIGS. 8A-8D compare the relative amounts of hyperproliferative tissue that developed over stent struts in rabbit iliac arteries over a period of 90 days when using a popular drug-eluting stent and a stent having the programmed coatings taught herein, according to some embodiments.

FIGS. 7A and 7B compare the relative amounts of endothelium that developed over stent struts in rabbit iliac arteries over a period of 2 weeks when using a popular drug-eluting stent and a stent having the programmed coatings taught herein, according to some embodiments.

MATERIALS AND METHODS: 14 Days Animal Experiment to Compare Functional Endothelization of SVTI EndoCoat™ to Competitive Drug Eluting Stent.

The EndoCoat™ was packaged and sterilized for implantation to compare to the competitive drug eluting stent. The rabbit was implanted with the SVTI EndoCoat™ and the competitive stent, with a stent in each of the pair of iliac arteries. All stents were 3.0 mm in diameter and 12 mm long (3.0×12 mm).

Implantation:

Anesthetized adult male New Zealand White rabbits underwent endothelial denudation of both iliac arteries using an angioplasty balloon catheter (3.0×10 mm, SVTI). Subsequently, a selected stent is deployed at a target stent-to-artery ratio of 1.3:1. A stent of a different design was deployed in the contralateral artery at the same level in the same fashion. Rabbits were anticoagulated with aspirin (40 mg/day) given orally 24 h before catheterization with continued dosing throughout the in-life phase of the study, whereas single dose intra-arterial heparin (150 IU/kg) will be administered at the time of catheterization. After device implantation, post-procedural angiography was performed to document vessel patency, and the animals were allowed to recover.

Follow-Up and Stent Harvest:

At 14 days after implantation, the rabbits were euthanized and the stents were explanted. The stented arteries will be perfused with 100-200 ml of ringers lactate prior and excised fresh. 5 mm of the artery extended from the ends of the stent will be transected and placed in a cryostat tube and snapped-frozen in liquid nitrogen and shipped on dry ice to a pathology laboratory for quantification of drug concentration.

The stented portions were immersion fixed in 10% NBF, placed in a 12-ml Falcon tube and shipped to pathology laboratory. For evaluation of endothelial cover-age, the stented arteries were bisected longitudinally with one half processed for scanning electron microscopy (SEM) and the opposite reserved for en face immunostaining of whole-mount vessels. The adjacent proximal and distal nonstented segments will serve as a positive control for immunostaining.

Morphometric Analysis of Endothelial Surface Coverage:

SEM images acquired at low power (15 magnification) will be gathered to provide a complete view of the entire luminal stent surface. The images were further enlarged (200 magnification), allowing direct visualization of endothelial cells. The extent of endothelial surface coverage on the stent struts will be traced and measured by morphometry software (Scope Image Plus). The results are expressed as a percentage of total surface area at each repeated crown along the longitudinal axis from proximal to distal orientation. Endothelial cells appeared as sheets of spindle or polygonal shaped mono-layers in close apposition. In contrast, intimal smooth muscle cells appeared as elongated processes and are generally stacked in disorganized or haphazard layers.

Immunostaining for Platelet-Endothelial Cell Adhesion Molecule (PECAM)-1 and Thrombomodulin (TM):

Both PECAM-1 and TM staining are key to evaluating the quality and functionality of the endothelium. Immunostaining of whole-mount specimens were incubated in an antibody cocktail containing primary antibodies against PECAM-1 (CD31, 1:20 dilution, Dako, Carpentaria, Calif.) and TM (1:10, American Diagnostica, Stamford, Conn.) at 4° C. Specific binding will be visualized using a secondary antibody cocktail consisting of donkey-antimouse Alexa Fluor 488 and donkey-antigoat Alexa Fluor 555 conjugate antibodies (1:200 dilution, Invitrogen Corp., Carlsbad, Calif.); TOTO-3 iodide served as a nuclear counterstain. The extent of endothelial coverage based on a positive reaction to PECAM-1 on the stent struts will be visually semi-quantified at 100 magnification for each level of struts and expressed as a mean percentage for the total area at each strut level for the entire stented surface. Thrombomodulin expression was assessed based on reaction intensity ranging from an absence to strong staining relative to nonadjacent control segments. Final confocal images were acquired in a multitrack mode in which separate green or red channels were scanned individually and then super-imposed using the Zeiss LSM software, thereby eliminating potential spectral overlap.

A cardiovascular pathologist and cardiologist examined the endothelial coverage of stent struts from SEM, the gap junctions from PECAM-1 staining, and TM expression to verify that EndoCoat™ endothelializes better than the leading marketed DES, and that drug concentrations in the vessel sections adjacent to the EndoCoat™ were at least 95% less than what was found for the competitive stent.

EXAMPLE 5

A Programmed Coating at Least Substantially Inhibits Restenosis

This example shows that the coatings taught herein at least substantially inhibit development of a restenosis when compared to a control development of such restenosis observed following implantation of a metal or polymer stent that does not elute a drug.

FIGS. 8A-8D compare the relative amounts of hyperproliferative tissue that developed over stent struts in rabbit iliac arteries over a period of 90 days when using a popular drug-eluting stent and a stent having the programmed coatings taught herein, according to some embodiments.

MATERIALS AND METHODS: 90 Days Chronic Animal Study to Compare Effectiveness of SVTI EndoCoat in Inhibiting restenosis Compared to Drug-Free stent (BMS) as control:

The EndoCoat™ stent was compared to the Bare Metal Stent (BMS) for effectiveness against restenosis in the rabbit iliac model. The rabbit was implanted with both the SVTI EndoCoat™ and the bare-metal stent (SVTI), with a stent in each of the pair of iliac arteries. All stents were 3.0×12 mm.

Implantation:

Anesthetized adult male New Zealand White rabbits underwent endothelial denudation of both iliac arteries using an angioplasty balloon catheter (3.0×10 mm, SVTI). Subsequently, a selected stent is deployed at a target stent-to-artery ratio of 1.3:1. A stent of a different design was deployed in the contralateral artery at the same level in the same fashion. Rabbits were anticoagulated with aspirin (40 mg/day) given orally 24 h before catheterization with continued dosing throughout the in-life phase of the study, whereas single dose intra-arterial heparin (150 IU/kg) will be administered at the time of catheterization. After device implantation, post-procedural angiography was performed to document vessel patency, and the animals were allowed to recover.

Follow-Up and Stent Harvest:

At 90 days the animal was euthanized and the stents were explanted. The excised, stented arteries were dehydrated in a graded series of ethanol and embedded in methylmethacrylate plastiC After polymerization, 2-3 mm sections from the proximal, mid, and distal portions of each single stent will be sectioned and stained with hematoxylin and eosin and an elastin (Movat pentachrome) stain. All sections will be examined by light microscopy for the presence of inflammation, thrombus, neointimal formation, and vessel wall injury. Morphometric measurements were performed to assess neointimal growth (thickness), as well as percentage stenosis based on area measurements.

We claim:

1. A therapeutic coating that promotes formation of a functional endothelium on a medical device, the coating comprising:
    a biodegradable, drug-containing inner layer that is positioned over a surface of a medical device and serves as a source of a drug that functions as an anti-proliferative agent in a subject; and,
    a biodegradable, outer layer positioned over a surface of the inner layer and comprising a polymer adapted to render the coating non-eluting beginning at time of implantation in the subject and continuing thereafter for a time period of about 20 to about 40 days, the polymer being further adapted to block release of the drug from the coating into the subject during the aforesaid time period to form a functional endothelium over the surface of the medical device, the functional endothelium providing a source of thrombomodulin to the subject;
    wherein the polymer is still further adapted to allow the drug to elute from the coating after the aforesaid time period;
    wherein the polymer has ester-terminal groups, a molecular weight ranging from about 50 KDaltons to about 190 KDaltons, the structure comprising P—CO2R, where P is the polymer backbone and R is an alkyl group having from 1 to 4 carbons;
    whereby the coating promotes development of the functional endothelium as the source of the thrombomodulin when compared to a control development of such endothelium formation observed following implantation of a metal drug-eluting medical device; and the coating inhibits development of a hyperproliferative tissue when compared to a control development of such hyperproliferative tissue observed following implantation of a metal medical device.

2. The coating of claim 1, wherein the medical device comprises a stent.

3. The coating of claim 1, wherein the drug-containing layer comprises a poly(lactic-co-glycolic acid), a monomer ratio of lactic acid to glycolic acid ranges from about 85:15 to about 50:50, and a molecular weight ranging from about 90 KDaltons to about 160 KDaltons.

4. The coating of claim 1, wherein the drug-retaining layer comprises a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

5. The coating of claim 1, wherein the thickness of the coating ranges from about 2 microns to about 9 microns.

6. The coating of claim 1, wherein the thickness ratio of the drug-retaining layer to the drug-containing layer ranges from about 4:1 to about 7:1.

7. The coating of claim 1 further comprising pockets of hydrophilic material in the drug-retaining layer, wherein the hydrophilic material comprises a component selected from the group consisting of dextran, heparin, ticlopidine, chlopidogrel, enoxaparin, dalteparin, hirudin, bivalirudin, argatroban, and danparoid.

8. The coating of claim 1, wherein the drug-reservoir layer further comprises an accelerant layer to accelerate the rate of elution, the accelerant layer having a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons.

9. A stent having a coating that promotes formation of a functional endothelium, the coating comprising:
- a biodegradable drug-containing inner layer that is positioned over a surface of the stent and serves as a source of a drug that functions as an anti-proliferative agent in a subject, wherein the drug-containing layer comprises a poly(lactic-co-glycolic acid), a monomer ratio of lactic acid to glycolic acid ranges from about 85:15 to about 50:50, and a molecular weight ranging from about 110 KDaltons to about 160 KDaltons; and,
- a biodegradable, outer layer positioned over a surface of the inner layer and comprising a polymer adapted to render the coating non-eluting beginning
- wherein, the drug retaining layer is void or substantially void of the drug at time of implantation in the subject and continuing thereafter for a time period of about 20 to about 40 days, the polymer being further adapted to, block release of the drug from the coating into the subject during the aforesaid time period to form a functional endothelium over the surface of the stent, the functional endothelium providing a source of thrombomodulin to the subject;
- wherein the polymer is still further adapted to allow the drug to elute from the coating after the aforesaid time period;
- wherein the drug-retaining layer comprises a poly(lactic-co-glycolic acid) polymer having ester terminal groups and the structure P—CO2R, where P is the polymer backbone and R is an alkyl group having from 1 to 4 carbons, a monomer ratio of lactic acid to glycolic acid ranging from about 85:15 to about 50:50, a molecular weight ranging from about 50 KDaltons to about 190 KDaltons, and a structure that remains at least substantially undegraded during an initial release of the drug from the coating;
- wherein the accelerant layer comprises a poly(lactic-co-glycolic acid) with acid terminal groups, a monomer ratio of lactic acid to glycolic acid that ranges from about 85:15 to about 50:50, a molecular weight that ranges from about 90 KDaltons to about 120 KDaltons, and functions to accelerate the rate of elution of drug from the coating;
- wherein the thickness ratio of the drug-reservoir layer to the drug-containing layer ranges from about 4:1 to about 10:1;
- whereby the coating promotes development of the functional endothelium as the source of the thrombomodulin when compared to a control development of such endothelium formation observed following implantation of a metal stent; and
- the coating inhibits development of a restenosis when compared to a control development of such restenosis observed following implantation of a metal stent.

10. The stent of claim 9, wherein the thickness of the coating ranges from about 2 microns to about 9 microns.

11. The stent of claim 9, wherein the thickness ratio of the drug-retaining layer to the drug-containing layer ranges from about 4:1 to about 7:1.

12. The stent of claim 9, further comprising pockets of hydrophilic material in the drug-retaining layer, wherein the hydrophilic material comprises a component selected from the group consisting of dextran, heparin, ticlopidine, chlopidogrel, enoxaparin, dalteparin, hirudin, bivalirudin, argatroban, and danparoid.

13. The stent of claim 9, wherein the drug is selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, batimistat, tranilast, transilast, halofuginon, acetylsalicylic acid, hirudin, steroids, ibuprofen, antimicrobials, antibiotics, actinomycin D, tissue plasma activators, estradiol, and transcription factor E2F1.

14. A medical device having a drug-retaining coating, comprising:
- a drug-containing, inner layer applied over a surface of the medical device, the drug-containing layer having a drug that functions as an anti-proliferative agent; and
- an outer layer applied over the inner layer and comprising a polymer adapted to render the drug-retaining coating non-eluting beginning at time of implantation in a subject and continuing thereafter for a time period of about 20 to about 40 days, the polymer being further adapted to block release of the drug from the coating into the subject during the aforesaid time period;
- wherein the polymer is still further adapted to allow the drug to elute from the coating after the aforesaid time period;
- whereby the coating promotes development of a functional endothelium as a source of thrombomodulin when compared to a control development of such endothelium formation observed following implantation of a metal medical device; and,
- the coating inhibits development of a hyperproliferative tissue when compared to a control development of such hyperproliferative tissue observed following implantation of a metal medical device.

* * * * *